US011655286B2

(12) United States Patent
Kyratsous et al.

(10) Patent No.: US 11,655,286 B2
(45) Date of Patent: May 23, 2023

(54) ANTI-PCRV ANTIBODIES THAT BIND PCRV, COMPOSITIONS COMPRISING ANTI-PCRV ANTIBODIES, AND METHODS OF USE THEREOF

(71) Applicant: REGENERON PHARMACEUTICALS, INC., Tarrytown, NY (US)

(72) Inventors: Christos Kyratsous, Irvington, NY (US); Alida Coppi, Flushing, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/898,193

(22) Filed: Jun. 10, 2020

(65) Prior Publication Data

US 2020/0392210 A1    Dec. 17, 2020

Related U.S. Application Data

(60) Provisional application No. 62/860,146, filed on Jun. 11, 2019.

(51) Int. Cl.
*C07K 16/12* (2006.01)
*A61P 31/04* (2006.01)
*A61K 39/40* (2006.01)
*A61K 45/06* (2006.01)
*A61K 39/00* (2006.01)

(52) U.S. Cl.
CPC .......... *C07K 16/1214* (2013.01); *A61K 39/40* (2013.01); *A61K 45/06* (2013.01); *A61P 31/04* (2018.01); *A61K 2039/505* (2013.01); *A61K 2039/507* (2013.01); *C07K 2317/21* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,596,556 A | 6/1986 | Morrow et al. |
| 4,790,824 A | 12/1988 | Morrow et al. |
| 4,941,880 A | 7/1990 | Burns |
| 4,946,778 A | 8/1990 | Ladner et al. |
| 5,064,413 A | 12/1991 | McKinnon et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,532,210 A | 7/1996 | Shen |
| 5,932,448 A | 8/1999 | Tso et al. |
| 6,096,002 A | 8/2000 | Landau |
| 6,129,914 A | 10/2000 | Weiner et al. |
| 6,329,511 B1 | 12/2001 | Vasquez et al. |
| 6,596,541 B2 | 7/2003 | Murphey et al. |
| 6,620,135 B1 | 9/2003 | Weston et al. |
| 7,294,754 B2 | 11/2007 | Poueymirou et al. |
| 7,576,259 B2 | 8/2009 | Poueymirou et al. |
| 7,582,298 B2 | 9/2009 | Stevens et al. |
| 7,659,442 B2 | 2/2010 | Poueymirou et al. |
| 8,246,995 B2 | 8/2012 | Dai et al. |
| 8,257,740 B1 | 9/2012 | Sung et al. |
| 8,502,018 B2 | 8/2013 | Murphy et al. |
| 9,416,171 B2 | 8/2016 | Lydon |
| 10,143,186 B2 | 12/2018 | McWhirter et al. |
| 2004/0101920 A1 | 5/2004 | Radziejewski et al. |
| 2008/0078000 A1 | 3/2008 | Poueymirou et al. |
| 2010/0331527 A1 | 12/2010 | Davis et al. |
| 2016/0024147 A1 | 1/2016 | Tustian et al. |

FOREIGN PATENT DOCUMENTS

| | | |
|---|---|---|
| EP | 2407537 A1 | 1/2012 |
| WO | WO2005103081 | 11/2005 |
| WO | WO2009088032 | 7/2009 |
| WO | WO2012122533 A2 | 9/2012 |
| WO | WO2013070615 | 5/2013 |
| WO | WO2014074528 A2 | 5/2014 |
| WO | WO2014121087 A1 | 8/2014 |
| WO | WO2017095744 A1 | 6/2017 |
| WO | WO2017134440 A2 | 8/2017 |
| WO | WO2018128973 A1 | 7/2018 |
| WO | WO2019067682 | 4/2019 |

OTHER PUBLICATIONS

Frank et al (The Journal of Infectious Diseases, 186:64-73, 2002).*
Baer et al (Infection and Immunity 77(3):1083-1090, 2009).*
Sawa et al (Human Vaccines & Immunotherapetics, 10(10:2843-2852, 2014).*
Ai-Lazikani et al. (1997) "Standard conformations for the canonical structures of immunoglobulins", J. Mol. Biol. 273:927-948.
Allen (1999) The Art, Science and Technology of Pharmaceutical Compounding.
Altschul et al. (1990) "Basic local alignment search tool", J. Mol. Biol., 215:403-410.
Altschul et al. (1997) "Gapped BLAST and PSI-BLAST: A New Generation of Protein Database Search Programs", NucleicAcids Res. 25:3389-3402.

(Continued)

*Primary Examiner* — Patricia Duffy
(74) *Attorney, Agent, or Firm* — FisherBroyles, LLP; Cara L. Crowley-Weber; Gabriele Amodeo

(57) ABSTRACT

The present disclosure provides antibodies and antigen-binding fragments of antibodies that bind to *Pseudomonas aeruginosa* PcrV, and methods of using the same. According to certain embodiments, the disclosure includes antibodies and antigen-binding fragments of antibodies that bind PcrV. The anti-PcrV antibodies and antigen-binding fragments are useful for the prevention and treatment of *P. aeruginosa* infections.

27 Claims, No Drawings

Specification includes a Sequence Listing.

(56) References Cited

OTHER PUBLICATIONS

Arruebo, et al. (2009) "Antibody-conjugated nanoparticles for biomedical applications" in J. Nanomat. vol. 2009, Article ID 439389, 24 pages, doi: 10.1155/2009/439389.

Baca, et al. (1997) "Antibody Humanization Using Monovalent Phage Display" J. Biol. Chem., 272:10678-10684.

Barbas, (1995) "Synthetic human antibodies", Nature Medicine 1:837-839.

Brennan, et al. (1985) "Preparation of bispecific antibodies by chemical recombination of monoclonal immunoglobulin G1 fragments", Science, 229:81-83.

Carpenter, et al. (2000) "Non-Fc Receptor-Binding Humanized Anti-CD3 Antibodies Induce Apoptosis of Activated Human T Cells", J. Immunol., 165:6205.

Carter (2001) "Bispecific human IgG by design", J. Immunol. Methods, 248:7-15.

Chothia, et al. (1989) "Conformations of immunoglobulin hypervariable regions", Nature, 342:877-883.

Conrath, et al. (2001) "Camel Single-domain Antibodies as Modular Building Units in Bispecific and Bivalent Antibody Constructs", J. Biol. Chem., 276:7346-7350.

De Bruin, et al. (1999) "Selection of high-affinity phage antibodies from phage display libraries", Nature Biotechnol., 17:397-399.

Dechiara, et al. (2009) "VelociMouse: fully ES cell derived F0-generation mice obtained from the injection of ES cells into eight-cell-stage embryos", Methods Mol Biol, 530:311-24.

Dechiara, et al. (2010) "Producing fully ES cell-derived mice from eight-cell stage embryo injections", Methods Enzymol, 476:285-94.

Desmyter, et al. (2001) "Antigen specificity and high affinity binding provided by one single loop of a camel single-domain antibody", J. Biol. Chem., 276:26285-26290.

Ehring (1999) "Hydrogen exchange/electrospray ionization mass spectrometry studies of structural features of proteins and protein/protein interactions.", Analytical Biochemistry, 267(2):252-259.

Engen and Smith (2001) "Investigating Protein Structure and Dynamics by Hydrogen Exchange MS", Anal. Chem., 73:256A-265A.

Everts, et al. (2002) "Selective Intracellular Delivery of Dexamethasone into Activated Endothelial Cells Using an E-Selectin-Directed Immunoconjugate", J. Immunol., 168:883-889.

Foote and Winter (1992) "Antibody framework residues affecting the conformation of the hypervariable loops", J. Mol. Biol., 224:487-499.

Francois, et al. (2012) "Safety and pharmacokinetics of an anti-PcrV PEGylated monoclonal antibody fragment in mechanically ventilated patients colonized with *Pseudomonas aeruginosa*: A randomized, double-blind, placebo-controlled trial", Crit. Care Med., 40: 2320-2326.

Gibellini, et al. (1998) "Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells", J. Immunol. 160:3891-3898.

Gonnet et al. (1992) "Exhaustive matching of the entire protein sequence database", Science, 25 6:1443-1445.

Good et al. (1991) "Historic Aspects of Intravenous Immunoglobulin Therapy", Cancer, 68: 1415-1421.

Harlow and Lane (2014) "Antibodies", (Cold Spring Harbor Press, Cold Spring Harbor, NY).

He, et al. (1998) "Humanization and Pharmacokinetics of a Monoclonal Antibody with Specificity for Both E- and P-Selectin", J. Immunol., 160:1029-1035.

Hoogenboom and Chames (2000) "Natural and designer binding sites made by phage display technology", Immunol. Today, 21:371-377.

Hsing and Bishop (1999) "Requirement for Nuclear Factor-κB Activation by a Distinct Subset of CD40-Mediated Effector Functions in B Lymphocytes", J. Immunol., 162:2804-2811.

Hudson and Kortt (1999) "High avidity scFv multimers; diabodies and triabodies", J. Immunol. Methods, 231:177-189.

International Search Report from PCT/2019/062370 dated Mar. 2, 2020, 19 pages.

Jendeberg, et al. (1997) "Engineering of Fc1 and Fc3 from human immunoglobulin G to analyse subclass specificity for *Staphylococcal* protein A", Journal of Immunological Methods, 201:25-34.

Junghans, et al. (1990) "Anti-Tac-H, a humanized antibody to the interleukin 2 receptor with new features for immunotherapy in malignant and immune disorders", Cancer Res., 50:1495-1502.

Kabat et al. (1991) "Sequences of Proteins of Immunological Interest", National Institutes of Health, Bethesda, Md.

Kaithamana, et al. (1999) "Induction of Experimental Autoimmune Graves' Disease in BALB/c Mice", J. Immunol., 163:5157-5164.

Kazane, et al. (2013) "Self-Assembled Antibody Multimers through Peptide Nucleic Acid Conjugation", J. Am. Chem. Soc. [Epub: Dec. 4, 2012].

Kim, et al. (2010) "IsdA and IsdB antibodies protect mice against *Staphylococcus aureus* abscess formation and lethal challenge", Vaccine, Elsevier, 28(38):6382-6392.

Klein, et al. (2012) "Progress in Overcoming the Chain Association Issue in Bispecific Heterodimeric IgG Antibodies", mAbs, 4:6, 1-11.

Kufer, et al. (2004) "A revival of bispecific antibodies", Trends Biotechnol., 22:238-244.

Langer (1990) "New methods of drug delivery", Science, 249:1527-1533.

Le Doussal, et al. (1991) "Enhanced in vivo targeting of an asymmetric bivalent hapten to double-antigen-positive mouse B cells with monoclonal antibody conjugate cocktails.", J. Immunol., 146:169-175.

Mack, et al. (1995) "A small bispecific antibody construct expressed as a functional single-chain molecule with high tumor cell cytotoxicity", Proc. Natl. Acad. Sci. USA, 92:7021-7025.

Malecki, et al. (2002) "Molecular immunolabeling with recombinant single-chain variable fragment (scFv) antibodies designed with metal-binding domains", Proc. Natl. Acad. Sci. USA, 99:213-218.

Marasco, et al. (2007) "The growth and potential of human antiviral monoclonal antibody therapeutics", Nature Biotechnology, 25: 1421-1434.

Martin et al. (1989) "Modeling antibody hypervariable loops: a combined algorithm", Proc. Natl. Acad. Sci. USA, 86:9268-9272.

Mendez, et al. (1997) "Functional transplant of megabase human immunoglobulin loci recapitulates human antibody response in mice", Nature Genetics, 15:146-156.

Menne, et al. (2000) "A comparison of signal sequence prediction methods using a test set of signal peptides", Bioinformatics Applications Note, 16: 741-742.

Meyaard, et al. (1997) "LAIR-1, a Novel Inhibitory Receptor Expressed on Human Mononuclear Leukocytes", Immunity 7:283-290.

Morrison (1985) "Transfectomas provide novel chimeric antibodies", Science, 229:1202-1207.

Padlan et al. (1995) "Identification of Specificity-Determining Residues in Antibodies", FASEB J., 9:133-139.

Pearson (1994) "Using the FASTA Program to Search Protein and DNA Sequence Databases", Methods Mol. Biol., 24:307-331.

Pearson (2000) "Flexible Sequence Similarity Searching with the FASTA3 Program Package", Methods Mol. Biol., 132:185-219.

Powell et al. (1998) "Compendium of excipients for parenteral formulations", PDA J. Pharm. Sci. Technol., 52:238-311.

Raso, et al. (1997) "Intracellular Targeting with Low pH-triggered Bispecific Antibodies", J. Biol. Chem., 272:27623.

Reddy et al. (2000) "Elimination of Fc Receptor-Dependent Effector Functions of a Modified IgG4 Monoclonal Antibody to Human CD4", J. Immunol., 164:1925-1933.

Reineke (2004) "Antibody Epitope Mapping Using Arrays of Synthetic Peptides", Methods Mol. Biol. 248: 443-63.

Segal, et al. (2001) "Introduction: bispecific antibodies", J. Immunol. Methods, 248:1-6.

Shield et al. (2002) "Lack of Fucose on Human IgG1 N-Linked Oligosaccharide Improves Binding to Human Fc γ RIII and Antibody-dependent Cellular Toxicity", JBC 277:26733-26740.

Smith, et al. (2015) "A novel, native-format bispecific antibody triggering T-cell killing of B-cells is robustly active in mouse tumor models and cynomolgus monkeys" Scientific Reports, 5:17943.

(56) References Cited

OTHER PUBLICATIONS

Tang, et al. (1999) "Use of a Peptide Mimotope to Guide the Humanization of MRK-16, an Anti-P-glycoprotein Monoclonal Antibody", J. Biol. Chem., 274:27371-27378.

Tustian, et al. (2016) "Development of purification process for fully human bispecific antibodies based upon modification of protein A binding avidity", MABS, 8(4):828-838.

Tomer, et al. (2000) "Characterization of a discontinuous epitope of the human immunodeficiency virus (HIV) core protein p24 by epitope excision and differential chemical modification followed by mass spectrometric peptide mapping analysis", Prot. Sci., 9: 487-496.

Traunecker, et al. (1991) "Bispecific single chain molecules (Janusins) target cytotoxic lymphocytes on HIV infected cells.", EMBO J., 10:3655-3659.

Tutt, et al. (1991) "Trispecific F (ab') 3 derivatives that use cooperative signaling via the TCR/CD3 complex and CD2 to activate and redirect resting cytotoxic T cells.", J. Immunol., 147:60-69.

Vajdos et al. (2002) "Comprehensive Functional Maps of the Antigen-Binding Site of an anti-ErbB2 Antibody Obtained With Shotgun Scanning Mutagenesis", J. Mol. Biol., 320:415-428.

Vaughan, et al. (1996) "Human Antibodies with Sub-nanomolar Affinities Isolated from a Large Non-immunized Phage Display Library", Nature Biotechnol., 14:309-314.

Volkel, et al. (2001) "Optimized linker sequences for the expression of monomeric and dimeric bispecific single-chain diabodies", Protein Engineering, 14:815-823.

Von Heijne (1983) "Patterns of Amino Acids near Signal-Sequence Cleavage Sites", Eur. J. Biochem., 133:17-21.

Von Heijne (1986) "A new method for predicting signal sequence cleavage sites", NucleicAcids Res., 14:4683-4690.

Wren, et al. (2002) "SIGNAL-Sequence Information and GeNomic AnaLysis", Comput. Methods Programs Biomed., 68:177-181.

Wright, et al. (2000) "Lymphoid/Neuronal Cell Surface OX2 Glycoprotein Recognizes a Novel Receptor on Macrophages Implicated in the Control of Their Function", Immunity, 13:233-242.

Wu et al. (1987) "Receptor-mediated in Vitro Gene Transformation by a Soluble DNA Carrier System", J. Biol. Chem., 262:4429-4432.

International Search Report and Written Opinion for PCT/2020/037008 dated Nov. 18, 2020, 20 pages.

* cited by examiner

SEQUENCE LISTING

<160> NUMBER OF SEQ ID NOS: 86

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1

```
gaggtgcagc tggtggagtc tgggggaggc ttggtacagc ctggagggtc cctgagactc      60
tcctgcgcag cctctggatt caccttcagt gatcatgaaa tgaattgggt ccgccaggct     120
ccagggaagg ggctggagtg gatttcatac attggtagtg gtgttgttac catgtactac     180
gcagactctg tgaggggccg attcaccatc tccagagaca acgccaagaa aacactgtat     240
ttgcaaatga acagcctgag agccgaggac acggctgttt attactgtgc gcagatcga      300 gggtattact ttggttcgga ggcctttcac tactggggcc agggaaccct ggtcaccgtc     360
``` tcctca                                                                366

```
<210> SEQ ID NO 2
<211> LENGTH: 122
<212> TYPE: PRT
<213> ORGANISM: Artificial Sequence
<220> FEATURE:
<223> OTHER INFORMATION: synthetic

<400> SEQUENCE: 2
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Glu Met Asn Trp Val Arg Gln Ala Pro Gly Lys Gly Leu Glu Trp Ile
        35                  40                  45

Ser Tyr Ile Gly Ser Gly Val Val Thr Met Tyr Tyr Ala Asp Ser Val
    50                  55                  60

Arg Gly Arg Phe Thr Ile Ser Arg Asp Asn Ala Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Gly Ser Glu Ala Phe His Tyr Trp
            100                 105                 110

Gly Gln Gly Thr Leu Val Thr Val Ser Ser
        115                 120

```
<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
```
ggattcacct tcagtgatca tgaa                                            24

```
<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4
```

Gly Phe Thr Phe Ser Asp His Glu
1               5

```
<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
```
attggtagtg gtgttgttac catg                                            24

```
<210> SEQ ID NO 6
<211> LENGTH: 8
<212> TYPE: PRT
<213> ORGANISM: Artificial Sequence
```

```
<220> FEATURE:
<223> OTHER INFORMATION: synthetic

<400> SEQUENCE: 6

Ile Gly Ser Gly Val Val Thr Met
1               5

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
gcgcgagatc gagggtatta ctttggttcg gaggcctttc actac              45

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Ala Arg Asp Arg Gly Tyr Tyr Phe Gly Ser Glu Ala Phe His Tyr
1               5                   10                  15

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccttccacc ctgtctgcat ctgtaggaga cagagtcacc     60
atcacttgtc gggccagtca gagtattagt aactggttgg cctggtatca gcagaaacca    120
gggaaagccc ctaagctcct gatctataag tcgtctagtt tagaaagtgg agtcccatca    180
aggttcagcg gcagtggatc tgggacagaa ttcactctca ccatcagcag cctacagcct    240
gatgattttg caacttatta ctgccaacag tataagagtt attcgctcac tttcggcgga    300
gggaccaagg tggagatcaa acga                                           324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ser Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys Gln Gln Tyr Lys Ser Tyr Ser Leu
            85                  90                  95

Thr Phe Gly Gly Gly Thr Lys Val Glu Ile Lys Arg
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagtatta gtaactgg                                                 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Asn Trp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 aagtcgtct                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Lys Ser Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtata agagttattc gctcact                                       27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr Lys Ser Tyr Ser Leu Thr
1               5

<210> SEQ ID NO 17
<211> LENGTH: 369
<212> TYPE: DNA
<213> ORGANISM: Artificial Sequence
<220> FEATURE:
<223> OTHER INFORMATION: synthetic

<400> SEQUENCE: 17

```
gaggtgcagc tggtggagtc tgggggagac ttggtacagc ctggggggtc cctgagactc      60
tcctgtaaag cctctggatt cacctttagc acctttgcca tgaactgggt ccgtcaggct     120
ccagggaggg gcctggagtg gtctcagct attggtgcta gtggttatag tacatactac     180
gtagactcca tgaagggccg cttcaccatc tccagagaca attccaagaa cacgctgtat     240
ctgcagatga acagcctggg agccgaggac acggccgtat attactgtgc gaaagaatat     300
agtgtctcgt caaactacta ctacggtatg gacgtctggg gccaagggac cacggtcacc     360
gtctcctca                                                              369
```

<210> SEQ ID NO 18
<211> LENGTH: 123
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Asp Leu Val Gln Pro Gly Gly
1               5                   10                  15

Ser Leu Arg Leu Ser Cys Lys Ala Ser Gly Phe Thr Phe Ser Thr Phe
            20                  25                  30

Ala Met Asn Trp Val Arg Gln Ala Pro Gly Arg Gly Leu Glu Trp Val
        35                  40                  45

Ser Ala Ile Gly Ala Ser Gly Tyr Ser Thr Tyr Tyr Val Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Glu Tyr Ser Val Ser Ser Asn Tyr Tyr Tyr Gly Met Asp Val
            100                 105                 110

Trp Gly Gln Gly Thr Thr Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19

```
ggattcacct ttagcaccctt tgcc                                             24
```

<210> SEQ ID NO 20
<211> LENGTH: 8
<212> TYPE: PRT
<213> ORGANISM: Artificial Sequence
<220> FEATURE:

```
<223> OTHER INFORMATION: synthetic

<400> SEQUENCE: 20

Gly Phe Thr Phe Ser Thr Phe Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attggtgcta gtggttatag taca                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Gly Ala Ser Gly Tyr Ser Thr
1               5

<210> SEQ ID NO 23
<211> LENGTH: 48
<212> TYPE: DNA
<213> ORGANISM: Artificial Sequence
<220> FEATURE:
<223> OTHER INFORMATION: synthetic

<400> SEQUENCE: 23
gcgaaagaat atagtgtctc gtcaaactac tactacggta tggacgtc                48

<210> SEQ ID NO 24
<211> LENGTH: 16
<212> TYPE: PRT
<213> ORGANISM: Artificial Sequence
<220> FEATURE:
<223> OTHER INFORMATION: synthetic

<400> SEQUENCE: 24

Ala Lys Glu Tyr Ser Val Ser Ser Asn Tyr Tyr Gly Met Asp Val
1               5                   10                  15

<210> SEQ ID NO 25
<211> LENGTH: 324
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc    60
atcacttgcc gggcaagtca gaccattagg agatatttaa attggtatca gcagaaagct   120
gggaaagccc ctaagctcct gatctatgct gcatccagtt tgttaagtgg cgtcccttca   180
aggttcagtg ccagtggatc tgggacagat ttcactctca ccatcagcag tctgcaacct   240
gaagattttt caacttacta ctgtcaacag acttacagta ttccgatcac cttcggccaa   300
gggacacgac tggagattaa acga                                         324
```

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Thr Ile Arg Arg Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Leu Ser Gly Val Pro Ser Arg Phe Ser Ala
50                  55                  60

Ser Gly Ser Gly Thr Asp Phe Thr Leu Thr Ile Ser Ser Leu Gln Pro
65                  70                  75                  80

Glu Asp Phe Ser Thr Tyr Tyr Cys Gln Gln Thr Tyr Ser Ile Pro Ile
                85                  90                  95

Thr Phe Gly Gln Gly Thr Arg Leu Glu Ile Lys Arg
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagaccatta ggagatat                                          18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

```
Gln Thr Ile Arg Arg Tyr
1               5
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                    9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser

-continued

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacagactt acagtattcc gatcacc                                        27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Thr Tyr Ser Ile Pro Ile Thr
1               5

<210> SEQ ID NO 33
<211> LENGTH: 369
<212> TYPE: DNA
<213> ORGANISM: Artificial Sequence
<220> FEATURE:
<223> OTHER INFORMATION: synthetic

<400> SEQUENCE: 33
gaggtgcagc tggtggagtc tgggggaggc ttggtacagc ctggggggtc cctgagactc      60
tcctgtgcag cctctggatt cacctttagc agctacgcca tgacctgggt ccgccaggct     120
ccagggaagg ggctggagtg ggtctcaagt attagaggta gtggttatag ttcagactac     180
gcagactccg tgaagggccg gttcaccatc tccagagaca attccgagaa cacggtttat     240
ctgcaaatga acagactgag agccgaggac acggccgttt attactgtgc gaaagagagg     300
tcagtgactg cctactacta ctacggtatg gacgtctggg gccaagggac cacggtcacc     360
gtctcctca                                                            369

<210> SEQ ID NO 34
<211> LENGTH: 123
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ser Ile Arg Gly Ser Gly Tyr Ser Ser Asp Tyr Ala Asp Ser Val
    50                  55                  60

Lys Gly Arg Phe Thr Ile Ser Arg Asp Asn Ser Glu Asn Thr Val Tyr
65                  70                  75                  80

Leu Gln Met Asn Arg Leu Arg Ala Glu Asp Thr Ala Val Tyr Tyr Cys
                85                  90                  95

Ala Lys Glu Arg Ser Val Thr Ala Tyr Tyr Tyr Gly Met Asp Val
            100                 105                 110

Trp Gly Gln Gly Thr Thr Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct ttagcagcta cgcc                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Ser Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagaggta gtggttatag ttca                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Arg Gly Ser Gly Tyr Ser Ser
1               5

<210> SEQ ID NO 39
<211> LENGTH: 48
<212> TYPE: DNA
<213> ORGANISM: Artificial Sequence
<220> FEATURE:
<223> OTHER INFORMATION: synthetic

<400> SEQUENCE: 39
gcgaaagaga ggtcagtgac tgcctactac tactacggta tggacgtc                48

<210> SEQ ID NO 40
<211> LENGTH: 16
<212> TYPE: PRT
<213> ORGANISM: Artificial Sequence
<220> FEATURE:
<223> OTHER INFORMATION: synthetic

<400> SEQUENCE: 40

Ala Lys Glu Arg Ser Val Thr Ala Tyr Tyr Tyr Tyr Gly Met Asp Val

<210> SEQ ID NO 41
<211> LENGTH: 324
<212> TYPE: DNA
<213> ORGANISM: Artificial Sequence
<220> FEATURE:
<223> OTHER INFORMATION: synthetic

<400> SEQUENCE: 41

```
gacatccagt tgacccagtc tccatccttc ctgtctgcat ctgtgggaga cagagtcacc    60
atcacttgct gggccagtca ggacattagc agttttttaa cctggtatca gcaaaagcca   120
gggatagccc ctaagctcct gatctatact gcatccactt tacaaagtgg ggtcccatca   180
aggttcagcg gcagtggatc tgggacagaa ttcactctca caatcagcag cctgcagcca   240
gaagattttg caacttatta ctgtcaacaa cttaaaagtt acccgctcac tttcggcgga   300
gggaccaagg tggagatcaa acga                                          324
```

<210> SEQ ID NO 42
<211> LENGTH: 108
<212> TYPE: PRT
<213> ORGANISM: Artificial Sequence
<220> FEATURE:
<223> OTHER INFORMATION: synthetic

<400> SEQUENCE: 42

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Phe
            20                  25                  30

Leu Thr Trp Tyr Gln Gln Lys Pro Gly Ile Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Lys Ser Tyr Pro Leu
                85                  90                  95

Thr Phe Gly Gly Gly Thr Lys Val Glu Ile Lys Arg
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43

```
caggacatta gcagtttt                                                  18
```

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Asp Ile Ser Ser Phe
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 actgcatcc                                                                 9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Thr Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacaactta aaagttaccc gctcact                                            27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Leu Lys Ser Tyr Pro Leu Thr
1               5

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggagac ttggtacagc cggggggtc cctgagactc         60 tcctgtgcag cctctggatt cacctttaac acctatgcca tgaattgggt ccgccaggct       120
ccagggaagg ggctggagtg gtcgcagtt attggtggta gtggttacag cacaaactac       180
gcagactccg tgaagggccg gttcaccatc tccagagaca attccaagaa cacgctgtat       240
ctgcaaatga acagcctgag gaccgaggac acggccgtat attactgtgc gaaagaaggg       300
aatatcgtgg ctctctactg gtacttcgat ctctggggcc gtggcaccct ggtcaccgtc       360
tcctca                                                                 366

<210> SEQ ID NO 50
<211> LENGTH: 122
<212> TYPE: PRT

<213> ORGANISM: Artificial Sequence
<220> FEATURE:
<223> OTHER INFORMATION: synthetic

<400> SEQUENCE: 50

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Val Ile Gly Gly Ser Gly Tyr Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Lys Glu Gly Asn Ile Val Ala Leu Tyr Trp Tyr Phe Asp Leu Trp
            100                 105                 110

Gly Arg Gly Thr Leu Val Thr Val Ser Ser
        115                 120
```

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct ttaacaccta tgcc                                            24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

```
Gly Phe Thr Phe Asn Thr Tyr Ala
1               5
```

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attggtggta gtggttacag caca                                            24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

```
Ile Gly Gly Ser Gly Tyr Ser Thr
1               5
```

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcgaaagaag ggaatatcgt ggctctctac tggtacttcg atctc     45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Lys Glu Gly Asn Ile Val Ala Leu Tyr Trp Tyr Phe Asp Leu
1               5                   10                  15

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgtaggaga cagagtcacc     60
atcacttgcc gggcaagtca gagcattagc agatatttaa attggtatca acagaaacca    120
gggaaagccc ctaagctcct gatctatgct gcatccagtt tgcaaggtgg ggtcccatca    180
aaattcagtg gcagtggatc tgggacagat ttcactctca ccatcagcag tctacaacct    240
gaagattttg caacttacta ctgtcaacag agttccacta ccccgctcac tttcggcgga    300
gggaccaagg tggagatcaa acga                                           324

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Thr Pro Leu
                85                  90                  95

Thr Phe Gly Gly Gly Thr Lys Val Glu Ile Lys Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagagcatta gcagatat                                                     18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Ser Ile Ser Arg Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                                9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacagagtt ccactacccc gctcact                                           27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ser Ser Thr Thr Pro Leu Thr
1               5

<210> SEQ ID NO 65
<211> LENGTH: 452
<212> TYPE: PRT

```
<213> ORGANISM: Artificial Sequence
<220> FEATURE:
<223> OTHER INFORMATION: synthetic

<400> SEQUENCE: 65
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | His |
| | | | 20 | | | | | 25 | | | | | 30 | | |
| Glu | Met | Asn | Trp | Val | Arg | Gln | Ala | Pro | Gly | Lys | Gly | Leu | Glu | Trp | Ile |
| | | 35 | | | | | 40 | | | | | 45 | | | |
| Ser | Tyr | Ile | Gly | Ser | Gly | Val | Val | Thr | Met | Tyr | Ala | Asp | Ser | Val |
| | 50 | | | | | 55 | | | | | 60 | | | | |
| Arg | Gly | Arg | Phe | Thr | Ile | Ser | Arg | Asp | Asn | Ala | Lys | Lys | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Asp | Arg | Gly | Tyr | Tyr | Phe | Gly | Ser | Glu | Ala | Phe | His | Tyr | Trp |
| | | | 100 | | | | | 105 | | | | | 110 | | |
| Gly | Gln | Gly | Thr | Leu | Val | Thr | Val | Ser | Ser | Ala | Ser | Thr | Lys | Gly | Pro |
| | | | 115 | | | | | 120 | | | | | 125 | | |
| Ser | Val | Phe | Pro | Leu | Ala | Pro | Ser | Ser | Lys | Ser | Thr | Ser | Gly | Gly | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | | 195 | | | | | 200 | | | | | 205 | | |
| His | Lys | Pro | Ser | Asn | Thr | Lys | Val | Asp | Lys | Lys | Val | Glu | Pro | Lys | Ser |
| | 210 | | | | | 215 | | | | | 220 | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | | 275 | | | | | 280 | | | | | 285 | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Asp | Glu | Leu | Thr | Lys | Asn | Gln | Val |
| | | | 355 | | | | | 360 | | | | | 365 | | |
| Ser | Leu | Thr | Cys | Leu | Val | Lys | Gly | Phe | Tyr | Pro | Ser | Asp | Ile | Ala | Val |
| | 370 | | | | | 375 | | | | | 380 | | | | |
| Glu | Trp | Glu | Ser | Asn | Gly | Gln | Pro | Glu | Asn | Asn | Tyr | Lys | Thr | Thr | Pro |

```
             385                 390                 395                 400
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450
```

<210> SEQ ID NO 66
<211> LENGTH: 214
<212> TYPE: PRT
<213> ORGANISM: Artificial Sequence
<220> FEATURE:
<223> OTHER INFORMATION: synthetic

<400> SEQUENCE: 66

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ser Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 67
<211> LENGTH: 453
<212> TYPE: PRT
<213> ORGANISM: Artificial Sequence
<220> FEATURE:
<223> OTHER INFORMATION: synthetic

<400> SEQUENCE: 67

```
Glu Val Gln Leu Val Glu Ser Gly Gly Asp Leu Val Gln Pro Gly Gly
1               5                   10                  15
```

-continued

```
Ser Leu Arg Leu Ser Cys Lys Ala Ser Gly Phe Thr Phe Ser Thr Phe
            20                  25                  30

Ala Met Asn Trp Val Arg Gln Ala Pro Gly Arg Gly Leu Glu Trp Val
            35                  40                  45

Ser Ala Ile Gly Ala Ser Gly Tyr Ser Thr Tyr Tyr Val Asp Ser Met
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Gly Ala Glu Asp Thr Ala Val Tyr Tyr Cys
                 85                  90                  95

Ala Lys Glu Tyr Ser Val Ser Ser Asn Tyr Tyr Gly Met Asp Val
                100                 105                 110

Trp Gly Gln Gly Thr Thr Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
```

```
                    435                 440                 445

Leu Ser Pro Gly Lys
        450

<210> SEQ ID NO 68
<211> LENGTH: 214
<212> TYPE: PRT
<213> ORGANISM: Artificial Sequence
<220> FEATURE:
<223> OTHER INFORMATION: synthetic

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Arg Arg Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Leu Ser Gly Val Pro Ser Arg Phe Ser Ala
    50                  55                  60

Ser Gly Ser Gly Thr Asp Phe Thr Leu Thr Ile Ser Ser Leu Gln Pro
65                  70                  75                  80

Glu Asp Phe Ser Thr Tyr Tyr Cys Gln Gln Thr Tyr Ser Ile Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 69
<211> LENGTH: 453
<212> TYPE: PRT
<213> ORGANISM: Artificial Sequence
<220> FEATURE:
<223> OTHER INFORMATION: synthetic

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ser Ile Arg Gly Ser Gly Tyr Ser Ser Asp Tyr Ala Asp Ser Val
    50                  55                  60
```

```
Lys Gly Arg Phe Thr Ile Ser Arg Asp Asn Ser Glu Asn Thr Val Tyr
 65                  70                  75                  80

Leu Gln Met Asn Arg Leu Arg Ala Glu Asp Thr Ala Val Tyr Tyr Cys
                 85                  90                  95

Ala Lys Glu Arg Ser Val Thr Ala Tyr Tyr Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 70
<211> LENGTH: 214
<212> TYPE: PRT
```

<213> ORGANISM: Artificial Sequence
<220> FEATURE:
<223> OTHER INFORMATION: synthetic

<400> SEQUENCE: 70

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Phe
            20                  25                  30

Leu Thr Trp Tyr Gln Gln Lys Pro Gly Ile Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Lys Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 452
<212> TYPE: PRT
<213> ORGANISM: Artificial Sequence
<220> FEATURE:
<223> OTHER INFORMATION: synthetic

<400> SEQUENCE: 71

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Val Ile Gly Gly Ser Gly Tyr Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Lys Glu Gly Asn Ile Val Ala Leu Tyr Trp Tyr Phe Asp Leu Trp
            100                 105                 110

```
Gly Arg Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 72
<211> LENGTH: 214
<212> TYPE: PRT
<213> ORGANISM: Artificial Sequence
<220> FEATURE:
<223> OTHER INFORMATION: synthetic

<400> SEQUENCE: 72

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Lys Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 454
<212> TYPE: PRT
<213> ORGANISM: Artificial Sequence
<220> FEATURE:
<223> OTHER INFORMATION: synthetic

<400> SEQUENCE: 73

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Glu Gly Leu Glu Trp Val
        35                  40                  45

Ser Ala Ile Thr Ile Ser Gly Ile Thr Ala Tyr Tyr Thr Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

-continued

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 74
<211> LENGTH: 214
<212> TYPE: PRT
<213> ORGANISM: Artificial Sequence
<220> FEATURE:
<223> OTHER INFORMATION: synthetic

<400> SEQUENCE: 74

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Val Ile
        35                  40                  45

Tyr Ser Ala Ser Thr Leu Gln Ser Gly Val Pro Ser Arg Phe Ser Gly
    50                  55                  60

```
Ser Gly Ser Gly Thr Asp Phe Thr Leu Ser Ile Ser Ser Leu Gln Pro
 65                  70                  75                  80

Asp Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 75
<211> LENGTH: 453
<212> TYPE: PRT
<213> ORGANISM: Artificial Sequence
<220> FEATURE:
<223> OTHER INFORMATION: synthetic

<400> SEQUENCE: 75

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Ser Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Asp Thr Asp Tyr Asn Ala Ala Phe Ile
     50                  55                  60

Ser Arg Leu Ser Ile Ser Lys Asp Asn Ser Lys Ser Gln Leu Phe Phe
 65                  70                  75                  80

Lys Met Asn Ser Leu Arg Ala Thr Asp Thr Ala Ile Tyr Tyr Cys Ala
                 85                  90                  95

Arg Asn Arg Gly Asp Ile Tyr Tyr Asp Phe Thr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205
```

-continued

Asn His Lys Pro Ser Asn Thr Lys Val Asp Lys Lys Val Glu Pro Lys
210             215                 220

Ser Cys Asp Lys Thr His Thr Cys Pro Pro Cys Pro Ala Pro Glu Leu
225             230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 76
<211> LENGTH: 214
<212> TYPE: PRT
<213> ORGANISM: Artificial Sequence
<220> FEATURE:
<223> OTHER INFORMATION: synthetic

<400> SEQUENCE: 76

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile Gln Asn Tyr
            20                  25                  30

Leu Ala Trp Tyr Gln Gln Thr Gln Gly Lys Ser Pro Gln Leu Leu Val
        35                  40                  45

Tyr Ser Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 77
<211> LENGTH: 294
<212> TYPE: PRT
<213> ORGANISM: Artificial Sequence
<220> FEATURE:
<223> OTHER INFORMATION: synthetic

<400> SEQUENCE: 77

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255
```

```
Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 78
<211> LENGTH: 300
<212> TYPE: PRT
<213> ORGANISM: Artificial Sequence
<220> FEATURE:
<223> OTHER INFORMATION: synthetic

<400> SEQUENCE: 78

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile His His His His His
            290                 295                 300

<210> SEQ ID NO 79
<211> LENGTH: 122
```

```
<212> TYPE: PRT
<213> ORGANISM: Artificial Sequence
<220> FEATURE:
<223> OTHER INFORMATION: synthetic

<400> SEQUENCE: 79
```

Lys Ala Leu Thr Ala Glu Leu Lys Val Tyr Ser Val Ile Gln Ser Gln
1               5                   10                  15

Ile Asn Ala Ala Leu Ser Ala Lys Gln Gly Ile Arg Ile Asp Ala Gly
            20                  25                  30

Gly Ile Asp Leu Val Asp Pro Thr Leu Tyr Gly Tyr Ala Val Gly Asp
        35                  40                  45

Pro Arg Trp Lys Asp Ser Pro Glu Tyr Ala Leu Leu Ser Asn Leu Asp
50                  55                  60

Thr Phe Ser Gly Lys Leu Ser Ile Lys Asp Phe Leu Ser Gly Ser Pro
65                  70                  75                  80

Lys Gln Ser Gly Glu Leu Lys Gly Leu Ser Asp Glu Tyr Pro Phe Glu
                85                  90                  95

Lys Asp Asn Asn Pro Val Gly Asn Phe Ala Thr Thr Val Ser Asp Arg
            100                 105                 110

Ser Arg Pro Leu Asn Asp Lys Val Asn Glu
        115                 120

```
<210> SEQ ID NO 80
<211> LENGTH: 128
<212> TYPE: PRT
<213> ORGANISM: Artificial Sequence
<220> FEATURE:
<223> OTHER INFORMATION: synthetic

<400> SEQUENCE: 80
```

Lys Ala Leu Thr Ala Glu Leu Lys Val Tyr Ser Val Ile Gln Ser Gln
1               5                   10                  15

Ile Asn Ala Ala Leu Ser Ala Lys Gln Gly Ile Arg Ile Asp Ala Gly
            20                  25                  30

Gly Ile Asp Leu Val Asp Pro Thr Leu Tyr Gly Tyr Ala Val Gly Asp
        35                  40                  45

Pro Arg Trp Lys Asp Ser Pro Glu Tyr Ala Leu Leu Ser Asn Leu Asp
50                  55                  60

Thr Phe Ser Gly Lys Leu Ser Ile Lys Asp Phe Leu Ser Gly Ser Pro
65                  70                  75                  80

Lys Gln Ser Gly Glu Leu Lys Gly Leu Ser Asp Glu Tyr Pro Phe Glu
                85                  90                  95

Lys Asp Asn Asn Pro Val Gly Asn Phe Ala Thr Thr Val Ser Asp Arg
            100                 105                 110

Ser Arg Pro Leu Asn Asp Lys Val Asn Glu His His His His His
        115                 120                 125

```
<210> SEQ ID NO 81
<211> LENGTH: 98
<212> TYPE: PRT
<213> ORGANISM: Artificial Sequence
<220> FEATURE:
<223> OTHER INFORMATION: synthetic

<400> SEQUENCE: 81
```

Lys Ala Leu Thr Ala Glu Leu Lys Val Tyr Ser Val Ile Gln Ser Gln
1               5                   10                  15

Ile Asn Ala Ala Leu Ser Ala Lys Gln Gly Ile Arg Ile Asp Ala Gly

```
                    20                  25                  30

Gly Ile Asp Leu Val Asp Pro Thr Leu Tyr Gly Tyr Ala Val Gly Asp
            35                  40                  45

Pro Arg Trp Lys Asp Ser Pro Glu Tyr Ala Leu Leu Ser Asn Leu Asp
     50                  55                  60

Thr Phe Ser Gly Lys Leu Ser Ile Lys Asp Phe Leu Ser Gly Ser Pro
 65                  70                  75                  80

Lys Gln Ser Gly Glu Leu Lys Gly Leu Ser Asp Glu Tyr Pro Phe Glu
                 85                  90                  95

Lys Asp

<210> SEQ ID NO 82
<211> LENGTH: 104
<212> TYPE: PRT
<213> ORGANISM: Artificial Sequence
<220> FEATURE:
<223> OTHER INFORMATION: synthetic

<400> SEQUENCE: 82

Lys Ala Leu Thr Ala Glu Leu Lys Val Tyr Ser Val Ile Gln Ser Gln
 1               5                  10                  15

Ile Asn Ala Ala Leu Ser Ala Lys Gln Gly Ile Arg Ile Asp Ala Gly
             20                  25                  30

Gly Ile Asp Leu Val Asp Pro Thr Leu Tyr Gly Tyr Ala Val Gly Asp
         35                  40                  45

Pro Arg Trp Lys Asp Ser Pro Glu Tyr Ala Leu Leu Ser Asn Leu Asp
     50                  55                  60

Thr Phe Ser Gly Lys Leu Ser Ile Lys Asp Phe Leu Ser Gly Ser Pro
 65                  70                  75                  80

Lys Gln Ser Gly Glu Leu Lys Gly Leu Ser Asp Glu Tyr Pro Phe Glu
                 85                  90                  95

Lys Asp His His His His His His
                100

<210> SEQ ID NO 83
<211> LENGTH: 454
<212> TYPE: PRT
<213> ORGANISM: Artificial Sequence
<220> FEATURE:
<223> OTHER INFORMATION: synthetic

<400> SEQUENCE: 83

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Thr Met Ser Gly Ile Thr Ala Tyr Tyr Thr Asp Asp Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Glu Phe Leu Pro Gly Thr His Tyr Tyr Tyr Gly Met Asp
                100                 105                 110

Val Trp Gly Gln Gly Thr Thr Val Thr Val Ser Ser Ala Ser Thr Lys
```

```
            115                 120                 125
Gly Pro Ser Val Phe Pro Leu Ala Pro Ser Ser Lys Ser Thr Ser Gly
        130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Leu Gly Thr Gln Thr Tyr Ile Cys Asn
        195                 200                 205
Val Asn His Lys Pro Ser Asn Thr Lys Val Asp Lys Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 84
<211> LENGTH: 214
<212> TYPE: PRT
<213> ORGANISM: Artificial Sequence
<220> FEATURE:
<223> OTHER INFORMATION: synthetic

<400> SEQUENCE: 84

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

```
                   20                  25                  30
Leu Gly Trp Tyr Gln Gln Lys Pro Gly Lys Ala Pro Lys Leu Leu Ile
            35                  40                  45

Tyr Ser Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 16
<212> TYPE: PRT
<213> ORGANISM: Artificial Sequence
<220> FEATURE:
<223> OTHER INFORMATION: synthetic

<400> SEQUENCE: 85

Ala Leu Ser Ala Lys Gln Gly Ile Arg Ile Asp Ala Gly Gly Ile Asp
1               5                   10                  15

<210> SEQ ID NO 86
<211> LENGTH: 21
<212> TYPE: PRT
<213> ORGANISM: Artificial Sequence
<220> FEATURE:
<223> OTHER INFORMATION: synthetic

<400> SEQUENCE: 86

Ser Gln Ile Asn Ala Ala Leu Ser Ala Lys Gln Gly Ile Arg Ile Asp
1               5                   10                  15

Ala Gly Gly Ile Asp
            20
```

ANTI-PCRV ANTIBODIES THAT BIND PCRV, COMPOSITIONS COMPRISING ANTI-PCRV ANTIBODIES, AND METHODS OF USE THEREOF

CROSS-REFERENCE TO RELATED APPLICATIONS

This application claims the benefit under 35 U.S.C. § 119(e) of U.S. Provisional Application Ser. No. 62/860,146, filed Jun. 11, 2019, which is herein specifically incorporated by reference in its entirety.

TECHNICAL FIELD

The present invention provides, in part, antibodies, bispecific antibodies, and antigen-binding fragments thereof, which specifically bind PcrV, as well as compositions and methods of treatment for *P. aeruginosa* infection.

SEQUENCE LISTING

An official copy of the sequence listing is submitted concurrently with the specification electronically via EFS-Web as an ASCII formatted sequence listing with a file name of "10494US01_SEQ_LIST_ST25.txt", a creation date of Jun. 10, 2020, and a size of about 76 KB. The sequence listing contained in this ASCII formatted document is part of the specification and is herein incorporated by reference in its entirety.

BACKGROUND

*Pseudomonas aeruginosa* (*P. aeruginosa*) is a Gram-negative *bacillus* present in a wide variety of environments. Requiring only simple nutrition, *P. aeruginosa* can grow in distilled water, and can grow well in acetate mediums and ammonium sulphate mediums. It can grow at temperatures as high as 42° C., and is resistant to high concentrations of salts, weak antiseptics, and many antibiotics.

An opportunistic pathogen, the bacteria are a major health concern, often drug resistant and causing community acquired and nosocomial infections. Such bacterial infections can be serious and life-threatening, with pneumonia being one of the most concerning manifestations. The bacterium rarely causes disease in healthy people and animals but is a significant problem for critically ill or immunocompromised individuals. For example, *P. aeruginosa* infection is a major problem in individuals who have cystic fibrosis (CF), resulting in progressive lung damage from recurrent and chronic respiratory tract infections with the bacterium. Others at risk include patients on mechanical ventilators, patients with tuberculosis, neutropenic cancer patients, and burn victims.

The bacterial type 3 secretion system (T3SS) is an important virulence factor of Gram-negative bacteria. T3SS is a complex multi-protein structure crossing the complete bacterial cell wall. Only two proteins are accessible to antibodies: the single barrel homopolymeric forming protein and the needle tip protein. *P. aeruginosa*'s V-tip protein (PcrV) is an example of a V-tip protein common to many Gram negative bacterial T3SSs. The PcrV is located at the end of the T3SS protein, forming a pentameric ring-type structure on the tip of the needle.

The T3SS hollow needle-like molecular structure operates by translocating toxins (ExoS, ExoT, ExoU, and ExoY) into eukaryotic cells, causing cell death and lysis. However, the translocation pore itself is sufficient to cause the death of infected cells, either directly through pore-mediated increases in membrane permeability, or indirectly through the activation of broad cellular defense responses. By killing white blood cells and epithelial cells and triggering inflammation, the T3SS virulence mechanism enables *P. aeruginosa* to evade human immune defenses.

There remains a significant unmet medical need for improved antibiotic drugs that treat or prevent *P. aeruginosa* infection.

SUMMARY

Provided herein are antibodies and antigen-binding fragments thereof that bind *P. aeruginosa*'s V-tip protein (PcrV). Such antibodies are useful for inhibiting or neutralizing the activity of the bacterial type 3 secretion system (T3SS) in *P. aeruginosa*. In some embodiments, the antibodies are useful for blocking translocation of toxins from the bacteria to the host cell and/or for preventing death of the host cells. In some embodiments, the antibodies function by blocking pore-mediated membrane permeability in the host cell.

In certain embodiments, the antibodies are useful in preventing, treating or ameliorating at least one symptom of *P. aeruginosa* infection in a subject. In certain embodiments, the antibodies may be administered prophylactically or therapeutically to a patient having, or at risk of acquiring, a *P. aeruginosa* infection. In certain embodiments, compositions containing at least one antibody of the disclosure may be administered to a patient having a *P. aeruginosa* infection. In certain embodiments, compositions containing at least one antibody of the disclosure may be administered to a patient at risk of contracting a *P. aeruginosa* infection, for example, a patient with cystic fibrosis, with diabetes, on a mechanical ventilator, undergoing surgery, with tuberculosis, with HIV, with a compromised immune system, with neutropenia, with an indwelling catheter, after physical trauma, with burns, in an intensive care unit, who is bed-ridden, with malignancy, with chronic obstructive pulmonary disease, in a long-term care health facility, or who is an intravenous drug user.

The antibodies provided herein can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In some aspects, the present disclosure provides isolated recombinant monoclonal antibodies or antigen-binding fragments thereof that bind specifically to PcrV. Such antibodies are often functional antagonists of the T3SS, i.e., the antibodies bind to PcrV and inhibits the T3SS.

In one embodiment, the present disclosure provides an isolated recombinant antibody or antigen-binding fragment thereof that specifically binds to PcrV, wherein the antibody has one or more of the following characteristics:

(a) comprises three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, and 50; and three light chain CDRs (LCDR1, LCDR2 and LCDR3) contained within any one of the light chain variable region (LCVR) sequences selected from the group consisting of SEQ ID NOs: 10, 26, 42, and 58;

(b) is a fully human monoclonal antibody;

(c) binds to full length PcrV with a dissociation constant ($K_D$) of less than $10^{-8}$M, as measured in a surface plasmon resonance assay at 25° C.;

(d) binds to full length PcrV with a dissociation constant ($K_D$) of less than $10^{-8}$M, as measured in a surface plasmon resonance assay at 37° C.;

(e) demonstrates neutralization of *P. aeruginosa* strain 6077 with an $IC_{50}$ ranging from about $10^{-11}$ M to about $10^{-8}$ M in a cytotoxicity assay;

(f) demonstrates neutralization of *P. aeruginosa* strain ATCC 700888 with an $IC_{50}$ ranging from about $10^{-9}$ M to about $10^{-7}$M in a cytotoxicity assay;

(g) demonstrates neutralization of *P. aeruginosa* strain 6077 with an $IC_{50}$ ranging from about $10^{-10}$M to about $10^{-6}$M in a hemolytic assay;

(h) demonstrates neutralization of *P. aeruginosa* strain ATCC 700888 with an $IC_{50}$ ranging from about $10^{-10}$M to about $10^{-7}$M in a hemolytic assay;

(i) decreases mortality from *P. aeruginosa* strain 6206 or strain 6077 in mice treated prophylactically with 5 mg/kg relative to untreated mice in an acute pneumonia model;

(j) decreases mortality from *P. aeruginosa* strain 6206 or strain 6077 in mice treated prophylactically with 1.0, 0.2 or 0.04 mg/kg relative to untreated mice in an acute pneumonia model;

(k) decreases lung bacterial burden of *P. aeruginosa* strain 6206 in mice treated prophylactically at 0.1 mg/kg or 0.2 mg/kg relative to untreated mice in an acute pneumonia model;

(l) decreases lung bacterial burden of *P. aeruginosa* strain PA01 in mice treated prophylactically at 25 mg/kg relative to untreated mice in an acute pneumonia model; and/or (m) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

In some aspects, the isolated antibody or antigen-binding fragment thereof further has one or more of the following characteristics:

(n) binds to full length PcrV (SEQ ID NO: 77) with an $EC_{50}$ of less than about $10^{-8}$M;

(o) binds to PcrV 136-233 (SEQ ID NO: 81) with an $EC_{50}$ of less than about $10^{-8}$M;

(p) interacts with at least one amino acid sequence selected from the group consisting of (i) amino acid residues ranging from about position 150 to about position 170 of SEQ ID NO: 78 and (ii) amino acid residues ranging from about position 155 to about 170 of SEQ ID NO: 78; and/or (q) interacts with at least one amino acid sequence selected from the group consisting of SEQ ID NO: 85 and SEQ ID NO: 86.

Exemplary anti-PcrV antibodies provided herein are listed in Tables 1, 2, and 3 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-PcrV antibodies. Table 2 sets forth the nucleic acid sequence identifiers of the HCVRs, LCVRs, HCDR1, HCDR2 HCDR3, LCDR1, LCDR2 and LCDR3 of the exemplary anti-PcrV antibodies. Table 3 provides the heavy chain and light chain nucleic acid and amino acid sequences of several exemplary antibodies.

Provided herein are antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto. In some aspects, the antibody or antigen-binding fragment thereof comprises an HCVR having an amino acid sequence selected from the group consisting of SEQ ID NOs: 2, 18, 34, and 50.

Also provided are antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto. In some aspects, the antibody or antigen-binding fragment thereof comprises an LCVR having an amino acid sequence selected from the group consisting of SEQ ID NOs: 10, 26, 42, and 58.

Provided herein are antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR amino acid sequence pair contained within any of the exemplary anti-PcrV antibodies listed in Table 1.

In one embodiment, the isolated antibody or antigen-binding fragment thereof comprises a HCVR/LCVR amino acid sequence pair selected from the group consisting of SEQ ID NOs: 2/10, 18/26, 34/42, and 50/58.

In one embodiment, the isolated antibody or antigen-binding fragment thereof comprises:

(a) a HCDR1 domain having an amino acid sequence selected from the group consisting of SEQ ID NOs: 4, 20, 36, and 52;

(b) a HCDR2 domain having an amino acid sequence selected from the group consisting of SEQ ID NOs: 6, 22, 38, and 54;

(c) a HCDR3 domain having an amino acid sequence selected from the group consisting of SEQ ID NOs: 8, 24, 40, and 56;

(d) a LCDR1 domain having an amino acid sequence selected from the group consisting of SEQ ID NOs: 12, 28, 44, and 60;

(e) a LCDR2 domain having an amino acid sequence selected from the group consisting of SEQ ID NOs: 14, 30, 46, and 62; and (f) a LCDR3 domain having an amino acid sequence selected from the group consisting of SEQ ID NOs: 16, 32, 48, and 64.

In certain embodiments, the HCVR/LCVR amino acid sequence pair is selected from the group consisting of SEQ ID NOs: 2/10 (H1H29329P), 18/26 (H1H29332P), 34/42 (H1H29336P), and 50/58 (H1H29339P).

Also provided herein are antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Also provided herein are antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Also provided herein are antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Also provided herein are antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Also provided herein are antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Also provided herein are antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Also provided herein are antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-PcrV antibodies listed in Table 1. In certain embodiments, the HCDR3/LCDR3 amino acid sequence pair is selected from the group consisting of SEQ ID NOs: 2/10 (H1H29329P), 18/26 (H1H29332P), 34/42 (H1H29336P), and 50/58 (H1H29339P).

Also provided herein are antibodies, or antigen-binding fragments thereof, comprising a set of six CDRs (i.e., HCDR1-HCDR2-HCDR3-LCDR1-LCDR2-LCDR3) contained within any of the exemplary anti-PcrV antibodies listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., H1H29329P), 20-22-24-28-30-32 (e.g., H1H29332P); 36-38-40-44-46-48 (e.g., H1H29336P); and 52-54-56-60-62-64 (e.g., H1H29339P).

In a related embodiment, provided herein are antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-PcrV antibodies listed in Table 1. For example, the present disclosure includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H1H29329P), 18/26 (e.g., H1H29332P), 34/42 (e.g., H1H29336P), and 50/58 (e.g., H1H29339P). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are antibodies having any one of the heavy chain amino acid sequences provided in Table 3 and/or any one of the light chain amino acid sequences provided in Table 3.

Provided herein are antibodies comprising an HC comprising an amino acid sequence selected from any of the HC amino acid sequences listed in Table 3, or a substantially similar sequence thereof having at least 90%, at least 95%, at least 98% or at least 99% sequence identity thereto.

Also provided are antibodies comprising an LC comprising an amino acid sequence selected from any of the LC amino acid sequences listed in Table 3, or a substantially similar sequence thereof having at least 90%, at least 95%, at least 98% or at least 99% sequence identity thereto.

Provided herein are antibodies comprising an HC and an LC amino acid sequence pair (HC/LC) comprising any of the HC amino acid sequences listed in Table 3 paired with any of the LC amino acid sequences listed in Table 3. According to certain embodiments, the present disclosure provides antibodies comprising an HC/LC amino acid sequence pair contained within any of the exemplary anti-PcrV antibodies listed in Table 3.

In one embodiment, the isolated antibody thereof comprises a HC/LC amino acid sequence pair selected from the group consisting of SEQ ID NOs: 65/66, 67/68, 69/70, and 71/72.

The present disclosure includes anti-PcrV antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Also provided herein are antibodies and antigen-binding fragments thereof that compete for specific binding to *P. aeruginosa* PcrV with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. In some aspects, the antibody or antigen-binding fragment thereof competes for binding to PcrV 136-233 (SEQ ID NO: 81) with the reference antibody or antigen-binding fragment thereof.

Further provided are antibodies and antigen-binding fragments thereof that bind the same *P. aeruginosa* PcrV epitope as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. In some aspects, the epitope comprises the residues of PcrV 136-233 (SEQ ID NO: 81) or the residues of PcrV 150-170 (SEQ ID NO: 86) or the residues of PcrV 155-170 (SEQ ID NO: 85).

Still further provided are isolated antibodies and antigen-binding fragments thereof that block *P. aeruginosa* PcrV translocation of toxins from the bacteria to a host cell. Still further provided are isolated antibodies and antigen-binding fragments thereof that block a T3SS pore-mediated increase in host cell membrane permeability.

In certain embodiments, the antibodies or antigen-binding fragments of the present disclosure are bispecific comprising a first binding specificity to a first epitope in the PcrV protein and a second binding specificity to a second epitope in the PcrV protein, wherein the first and second epitopes are distinct and non-overlapping. In certain embodiments the bispecific may comprise a first arm that binds to an epitope in the PcrV protein and a second arm that binds to a different *P. aeruginosa* antigen.

In another aspect, provided herein are nucleic acid molecules encoding anti-PcrV antibodies or portions thereof. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

Also provided herein are nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

Also provided herein are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-PcrV antibodies listed in Table 1.

Also provided herein are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-PcrV antibodies listed in Table 1.

Also provided herein are nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same PcrV antibody listed in Table 1.

Also provided herein are nucleic acid molecules encoding any of the heavy chain amino acid sequences listed in Table 1. The present disclosure also provides nucleic acid molecules encoding any of the light chain amino acid sequences listed in Table 1.

In a related aspect, provided herein are recombinant expression vectors capable of expressing a polypeptide comprising a heavy or light chain variable region of an anti-PcrV antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, provided herein is a pharmaceutical composition comprising one or more isolated monoclonal antibodies or antigen-binding fragments thereof which specifically bind to PcrV as disclosed herein and a pharmaceutically acceptable carrier or diluent. The one or more isolated antibodies can comprise the CDRs within an HCVR/LCVR amino acid sequence pair selected from the group consisting of the HCVR and LCVR sequences listed in Table 1. The one or more isolated antibodies can comprise an HCVR/LCVR amino acid sequence pair comprising the HCVR and LCVR sequences listed in Table 1. In one embodiment, the HCVR/LCVR amino acid sequence pair is selected from the group consisting of SEQ ID NOs: 2/10, 18/26, 34/42, and 50/58. In one embodiment, the HCVR/LCVR amino acid sequence pair is selected from the group consisting of SEQ ID NOs: 34/42 and 50/58.

In another related aspect, provided herein is a composition, which is a combination of an anti-PcrV antibody and one or more additional therapeutic agents.

In one embodiment, the additional therapeutic agent is any agent that is advantageously combined with an anti-PcrV antibody. Exemplary agents that may be advantageously combined with an anti-PcrV antibody include, without limitation, other agents that bind and/or inhibit *P. aeruginosa* activity (including other antibodies or antigen-binding fragments thereof, etc.) and/or agents which do not directly bind PcrV or another *P. aeruginosa* antigen but nonetheless inhibit bacterial activity including infectivity of host cells. In some aspects, the second therapeutic agent may be a therapeutic for treating infections associated with a different organism which may co-infect with *P. aeruginosa*, for example, an organism such as *S. aureus*. In some aspects, the additional therapeutic agent is selected from the group consisting of an antibiotic, an anti-inflammatory drug, a different antibody to *P. aeruginosa*, and a therapeutic useful for treating a co-infection. In some aspects, the additional therapeutic agent is useful for treating a *S. aureus* co-infection.

In a related aspect, provided herein is a method of neutralizing *P. aeruginosa*, the method comprising exposing a cell containing intracellular *P. aeruginosa* to a composition comprising one or more anti-PcrV antibodies or antigen-binding fragments thereof, wherein the exposing results in enhanced protection from cell death. In certain embodiments, the exposing may be in vitro or in vivo. In certain embodiments, the enhanced protection is observed when the antibody is used alone, or when it is used in combination with one or more additional therapeutic agents or antibodies against *P. aeruginosa*. In certain embodiments, the one or more additional therapeutic agents is selected from the group consisting of an antibiotic, an anti-inflammatory drug, a different antibody to *P. aeruginosa*, and a therapeutic useful for treating a co-infection. In some aspects, the one or more additional therapeutic agents is a therapeutic useful for treating a co-infection such as a *S. aureus* infection. In some aspects, the one or more additional therapeutic agents is a different anti-*P. aeruginosa* antibody.

In some embodiments, provided herein are methods of decreasing the risk of acquiring *P. aeruginosa* infection. In some aspects, the method comprises administering one or more anti-PcrV antibodies provided herein, or a pharmaceutical composition comprising one or more anti-PcrV antibodies. A patient at greater risk for *P. aeruginosa* infection can be a patient with cystic fibrosis, with diabetes, on a mechanical ventilator, undergoing surgery, with tuberculosis, with HIV, with a compromised immune system, with neutropenia, with an indwelling catheter, after physical trauma, with burns, in an intensive care unit, who is bedridden, with malignancy, with chronic obstructive pulmonary disease, in a long-term care health facility, or who is an intravenous drug user.

In certain embodiments, provided herein are methods of decreasing bacterial load in a subject. In certain embodiments, decreasing bacterial load is apparent in a subject's lung. In some aspects, the method comprises administering to the subject a composition comprising one or more antibodies or antigen-binding fragments thereof that bind PcrV. In some aspects, the antibody or antigen-binding fragment thereof blocks *P. aeruginosa* delivery of toxins into the host cell. In some aspects, treatment with an anti-PcrV antibody provided herein decreases *P. aeruginosa* bacterial load. In some aspects, treatment with an anti-PcrV antibody provided herein decreases *P. aeruginosa* bacterial load and *S. aureus* bacterial load.

In some embodiments, provided herein are methods of increasing the survival, or the likelihood of survival, of a subject suffering from infection with *P. aeruginosa*, or a subject at risk for *P. aeruginosa* infection. In some aspects, the method comprises administering at least one anti-PcrV antibody or antigen-binding fragment thereof provided herein, or a pharmaceutical composition comprising at least one anti-PcrV antibody, to a subject in need thereof.

In some embodiments, provided herein are methods of increasing the survival, or the likelihood of survival, of a subject suffering from infection with *P. aeruginosa*, or a subject at risk for *P. aeruginosa* infection, wherein the subject suffers from cystic fibrosis. In some aspects, the method comprises administering at least one anti-PcrV antibody or antigen-binding fragment thereof provided herein, or a pharmaceutical composition comprising at least one anti-PcrV antibody, to the subject. In some aspects, the subject does not have pneumonia symptoms at the time of administration.

In some embodiments, provided herein are methods to ameliorate or reduce the severity, duration, or frequency of occurrence, of at least one symptom of a *P. aeruginosa* infection in a subject. In some aspects, the method comprises administering one or more anti-PcrV antibodies or antigen-binding fragments provided herein, or a pharmaceutical composition comprising at least one anti-PcrV antibody or antigen-binding fragment thereof, to a subject in need thereof. In some aspects, the at least one symptom is selected from the group consisting of fever, chills, headache, fatigue, joint pain, stiffness, myalgia, diarrhea, and vomiting; pain, itching, and liquid discharge in the ears; rashes, including pus-filled pimples on the skin; pain and redness in an eye; pneumonia, coughing, and congestion; soft tissue discharge of green pus and a sweet, fruity smell; and urinary tract infection.

In some aspects, the subject has pneumonia, bacteremia, a bone infection, a joint infection, a skin infection, a burn infection, a wound infection, or any combination thereof, caused by *P. aeruginosa* infection.

In some aspects, the one or more anti-PcrV antibodies or antigen-binding fragments thereof provided herein, or the pharmaceutical composition comprising at least one anti-PcrV antibody or antigen-binding fragment thereof, is administered prophylactically or therapeutically to the subject in need thereof to treat or prevent the development of invasive infection with *P. aeruginosa*.

In one embodiment, the subject in need thereof is a subject with an active *P. aeruginosa* infection or a subject at risk for acquiring *P. aeruginosa* infection. In some aspects, the subject is selected from the group consisting of an immunocompromised individual, a hospitalized individual, an individual suffering from a major illness, an individual undergoing surgery, an individual undergoing an invasive procedure, a trauma patient, an intravenous drug user, an individual with severe burns, an individual using a breathing machine, an individual with a catheter, an individual receiving chemotherapy, an individual with diabetes, an individual with cystic fibrosis, an individual with HIV, an individual with tuberculosis, or an individual with any other medical condition that can compromise the immune system. In some aspects, the subject has a *P. aeruginosa* infection. In some aspects, the subject has a *P. aeruginosa* infection and a *S. aureus* infection. In some aspects, the subject has a *P. aeruginosa* infection and one or more other gram-negative or gram-positive co-infections. In some aspects, the subject has pneumonia, bacteremia, a bone infection, a joint infection, a skin infection, a burn infection, a wound infection, or any combination thereof, caused by *P. aeruginosa* infection. In some aspects, the *P. aeruginosa* is resistant or partially resistant to an antibiotic.

In one embodiment, the subject in need thereof may be administered at least one anti-PcrV antibody or an antigen-binding fragment thereof as provided herein, or a pharmaceutical composition comprising at least one antibody or antigen-binding fragment thereof, in combination with one or more additional therapeutic agents. The one or more additional therapeutic agents may be selected from the group consisting of an antibiotic, an anti-inflammatory drug (such as corticosteroids, and non-steroidal anti-inflammatory drugs), a different antibody to *P. aeruginosa*, a therapeutic useful for treating a co-infection such as a *S. aureus* infection, and any other drug or therapy known in the art useful for ameliorating at least one symptom of a *P. aeruginosa* infection, or for reducing the bacterial load in a patient. In one embodiment, the one or more additional therapeutic agents comprise one or more anti-PcrV antibodies. In certain embodiments, the second therapeutic agent may be an agent that helps to counteract or reduce any possible side effect(s) associated with an antibody or antigen-binding fragment thereof of the disclosure, if such side effect(s) should occur.

In one embodiment, the pharmaceutical composition may be administered subcutaneously, intravenously, intradermally, intramuscularly, intranasally, or orally.

In certain embodiments, the one or more antibodies or antigen-binding fragments thereof may be administered prophylactically or therapeutically to a subject having, or at risk of having, or pre-disposed to developing a *P. aeruginosa* infection. The subjects at risk include, but are not limited to, an immunocompromised individual, a hospitalized individual, an individual suffering from a major illness, an individual undergoing surgery or another invasive procedure, a trauma patient, an intravenous drug user, an individual with severe burns, an individual using a breathing machine, an individual with a catheter, an individual receiving chemotherapy, an individual with tuberculosis, an individual with diabetes, an individual with cystic fibrosis, an individual with HIV, or an individual with any other medical condition that can compromise the immune system.

The present disclosure also includes an anti-PcrV antibody or antigen-binding fragment thereof as provided herein for use in treating a subject who has, or is at risk of acquiring, *P. aeruginosa* infection, or for use in the manufacture of a medicament for the treatment of a disease or disorder associated with a *P. aeruginosa* infection.

Provided herein are injection devices (e.g., hypodermic needle and syringe, an autoinjector or a pre-filled syringe) or vessels (e.g., a vial) that include an anti-PcrV antibody or antigen-binding fragment thereof as provided herein (e.g., an antibody having an HCVR/LCVR amino acid sequence pair is selected from the group consisting of SEQ ID NOs: 2/10, 18/26, 34/42, and 50/58).

Further provided are methods for administering the composition to a subject (e.g., a human) including the step of introducing the components of the composition into the body of the subject, e.g., parenterally, for example, by injection using an injection device. In an embodiment of the disclosure, the subject suffers from a *P. aeruginosa* infection or is at risk of acquiring a *P. aeruginosa* infection.

Further provided are methods for making a composition comprising the anti-PcrV antibody (e.g., a composition comprising an antibody having an HCVR/LCVR amino acid sequence pair is selected from the group consisting of SEQ ID NOs: 2/10, 18/26, 34/42, and 50/58) and a pharmaceutically acceptable carrier.

Also provided are methods of making the device or vessel that comprises a composition disclosed herein comprising introducing the components of the combination into the vessel or device.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described.

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-PcrV monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies disclosed herein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

Also contemplated herein are fully human anti-PcrV monoclonal antibodies comprising variants of any of the HCVR, LCVR, and/or CDR amino acid sequences disclosed herein having one or more conservative substitutions. For example, the present disclosure includes anti-PcrV antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the disclosure created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-7}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to PcrV. Moreover, multi-specific antibodies that bind to P. aeruginosa PcrV and one or more additional P. aeruginosa antigens or a bi-specific that binds to two different regions of P. aeruginosa PcrV are nonetheless considered antibodies that "specifically bind", as used herein.

The term "high affinity" antibody refers to those mAbs having a binding affinity to PcrV, expressed as $K_D$, of at least $10^{-7}$ M; preferably $10^{-8}$ M; more preferably $10^{-9}$ M, even more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from PcrV with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PcrV.

In specific embodiments, antibody or antibody fragments of the disclosure may be conjugated to a moiety such a ligand or a therapeutic moiety ("immunoconjugate"), such as an antibiotic, a second anti-*P. aeruginosa* antibody, or any other therapeutic moiety useful for treating a *P. aeruginosa* infection.

An "isolated antibody", as used herein, is intended to refer to an antibody that is substantially free of other antibodies (Abs) having different antigenic specificities (e.g., an isolated antibody that specifically binds *P. aeruginosa* PcrV, or a fragment thereof, and is substantially free of Abs that specifically bind antigens other than PcrV).

A "blocking antibody" or a "neutralizing antibody", as used herein (or an "antibody that neutralizes *P. aeruginosa* activity" or "antagonist antibody"), is intended to refer to an antibody whose binding to PcrV results in inhibition of at least one biological activity of *P. aeruginosa*. For example, an antibody of the disclosure may prevent or block *P. aeruginosa* bacteria from translocating bacterial toxins into a host cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-bacterial agents upon appropriate formulation, or in association with active vaccination, or as a diagnostic tool.

"Antibody-dependent cell-mediated cytotoxicity" or "ADCC" is a mechanism of cell-mediated immune defense whereby an effector cell of the immune system actively lyses a target cell, whose membrane-surface antigens have been bound by specific antibodies, such as by those described herein. As such, it is one mechanism through which, for example, a bacteria specific antibody can act to limit the spread of infection. Classical ADCC is mediated by natural killer cells (NK cells), macrophages, neutrophils and in certain instances, eosinophils.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference anti-PcrV antibody of the disclosure, the reference antibody is allowed to bind to PcrV protein under saturating conditions. Next, the ability of a test antibody to bind to the PcrV protein is assessed. If the test antibody is able to bind to PcrV protein following saturation binding with the reference anti-PcrV antibody, it can be concluded that the test antibody binds to a different epitope than the reference anti-PcrV antibody. On the other hand, if the test antibody is not able to bind to the PcrV protein following saturation binding with the reference anti-PcrV antibody, then the test antibody may bind to the same epitope as the epitope bound by the reference anti-PcrV antibody.

Typically, an antibody or antigen-binding fragment provided herein which is modified in some way retains the ability to specifically bind to PcrV, e.g., retains at least 10% of its PcrV binding activity (when compared to the parental antibody) when that activity is expressed on a molar basis. In some aspects, an antibody or antigen-binding fragment of the disclosure retains at least 20%, 50%, 70%, 80%, 90%, 95% or 100% or more of the PcrV binding affinity as the parental antibody. It is also intended that an antibody or antigen-binding fragment of the present disclosure can include conservative or non-conservative amino acid substitutions (referred to as "conservative variants" or "function conserved variants" of the antibody) that do not substantially alter its biologic activity.

A "variant" of a polynucleotide refers to a polynucleotide comprising a nucleotide sequence that is at least about 70-99.9% (e.g., at least about 70, 72, 74, 75, 76, 79, 80, 81, 82, 83, 84, 85, 86, 87, 88, 89, 90, 91, 92, 93, 94, 95, 96, 97, 98, 99, 99.5, or 99.9%) identical to a referenced nucleotide sequence that is set forth herein (e.g., SEQ ID NO: 1, 9, 17, 25, 33, 41, 49, or 57); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

A "variant" of a polypeptide, such as an immunoglobulin chain (e.g., H1H29329P $V_H$, $V_L$, HC, or LC, H1H29332P $V_H$, $V_L$, HC, or LC, H1H29336P $V_H$, $V_L$, HC, or LC, or H1H29339P $V_H$, $V_L$, HC, or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 10, 65, 66, 18, 26, 67, 68, 34, 42, 69, 70, 50, 58, 71, or 72); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservatively modified variant" or a "conservative substitution" refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to significantly disrupt biological activity.

In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson (1994) Methods Mol. Biol. 24: 307-331). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402.

Anti-PcrV antigen-binding proteins, e.g., antibodies and antigen-binding fragments thereof of the present disclosure, in one embodiment, include a heavy chain immunoglobulin variable region having at least 70% (e.g., 80%, 85%, 90%, 95%, 99%) amino acid sequence identity to the amino acids set forth in SEQ ID NO: 2, 18, 34, or 50; and/or a light chain immunoglobulin variable region having at least 70% (e.g., 80%, 85%, 90%, 95%, 99%) amino acid sequence identity to the amino acids set forth in SEQ ID NO: 10, 26, 42, or 58.

In addition, a variant anti-PcrV antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), nonsense mutations, deletions, or insertions. For example, the present disclosure includes antigen-binding proteins which include an immunoglobulin heavy chain variant comprising the amino acid sequence set forth in SEQ ID NO: 2, 18, 34, or 50 but having one or more of such mutations and/or an immunoglobulin light chain variant comprising the amino acid sequence set forth in SEQ ID NO: 10, 26, 42, or 58 but having one or more of such mutations. In an embodiment of the disclosure, a variant anti-PcrV antigen-binding protein includes an immunoglobulin heavy chain variant comprising HCDR1, HCDR2, and HCDR3 wherein one or more (e.g., 1 or 2 or 3) of such CDRs has one or more of such mutations (e.g., conservative substitutions) and/or an immunoglobulin light chain variant comprising LCDR1, LCDR2, and LCDR3 wherein one or more (e.g., 1 or 2 or 3) of such CDRs has one or more of such mutations (e.g., conservative substitutions).

The disclosure further provides variant anti-PcrV antigen-binding proteins, e.g., antibodies or antigen-binding fragments thereof, comprising one or more variant CDRs (e.g., any one or more of HCDR1, HCDR2, HCDR3, LCDR1, LCDR2, and/or LCDR3) that are set forth herein with at least 70%, 75%, 80%, 85%, 90%, 95%, 98%, 99% or 99.9% sequence identity or similarity to, e.g., SEQ ID NO: 4, 6, 8, 12, 14, and/or 16; or 20, 22, 24, 28, 30, and/or 32; or 36, 38, 40, 44, 46, and/or 48; or 52, 54, 56, 60, 62, and/or 64.

Embodiments of the present disclosure also include variant antigen-binding proteins, e.g., anti-PcrV antibodies and antigen-binding fragments thereof, that comprise immunoglobulin $V_H$s and $V_L$s, or HCs and LCs, which comprise an amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the HCDR1, HCDR2, HCDR3, LCDR1, LCDR2, and/or LCDR3 of such immunoglobulins are not variants and comprise the amino acid sequence set forth in SEQ ID NO: 4, 6, 8, 12, 14, and/or 16; or 20, 22, 24, 28, 30, and/or 32; or 36, 38, 40, 44, 46, and/or 48; or 52, 54, 56, 60, 62, and/or 64, respectively. Thus, in such embodiments, the CDRs within variant antigen-binding proteins are not, themselves, variants.

Function-conservative variants of the anti-PcrV antibodies and antigen-binding fragments thereof are also part of the present invention. Any of the variants of the anti-PcrV antibodies and antigen-binding fragments thereof (as discussed herein) may be "function-conservative variants". Such function-conservative variants may, in some cases, also be characterized as conservatively modified variants. "Function-conservative variants," as used herein, refers to variants of the anti-PcrV antibodies or antigen-binding fragments thereof in which one or more amino acid residues have been changed without significantly altering one or more functional properties of the antibody or fragment. In an embodiment of the invention, a function-conservative variant of an anti-PcrV antibody or antigen-binding fragment thereof of the present disclosure comprises a variant amino acid sequence and exhibits one or more of the following functional properties:

binds to full length PcrV with a dissociation constant ($K_D$) of less than $10^{-8}$M, as measured in a surface plasmon resonance assay at 25° C.;

binds to full length PcrV with a dissociation constant ($K_D$) of less than $10^{-8}$M, as measured in a surface plasmon resonance assay at 37° C.;

demonstrates neutralization of *P. aeruginosa* strain 6077 with an $IC_{50}$ ranging from about $10^{-11}$ M to about $10^{-8}$ M in a cytotoxicity assay;

demonstrates neutralization of *P. aeruginosa* strain ATCC 700888 with an $IC_{50}$ ranging from about $10^{-9}$ M to about $10^{-7}$M in a cytotoxicity assay;

demonstrates neutralization of *P. aeruginosa* strain 6077 with an $IC_{50}$ ranging from about $10^{-10}$ M to about $10^{-6}$M in a hemolytic assay;

demonstrates neutralization of *P. aeruginosa* strain ATCC 700888 with an $IC_{50}$ ranging from about $10^{-10}$ M to about $10^{-7}$M in a hemolytic assay;

decreases mortality from *P. aeruginosa* strain 6206 or strain 6077 in mice treated prophylactically with 5 mg/kg relative to untreated mice in an acute pneumonia model;

decreases mortality from *P. aeruginosa* strain 6206 or strain 6077 in mice treated prophylactically with 1.0, 0.2 or 0.04 mg/kg relative to untreated mice in an acute pneumonia model;

decreases lung bacterial burden of *P. aeruginosa* strain 6206 in mice treated prophylactically at 0.1 mg/kg or 0.2 mg/kg relative to untreated mice in an acute pneumonia model;

decreases lung bacterial burden of *P. aeruginosa* strain PA01 in mice treated prophylactically at 25 mg/kg relative to untreated mice in an acute pneumonia model; and/or cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1;

binds to full length PcrV (SEQ ID NO: 77) with an $EC_{50}$ of less than about $10^{-8}$ M;

binds to PcrV 136-233 (SEQ ID NO: 81) with an $EC_{50}$ of less than about $10^{-8}$ M;

interacts with amino acid residues ranging from about position 150 to about position 170 of SEQ ID NO: 78;

interacts with amino acid residues ranging from about position 155 to about 170 of SEQ ID NO: 78; and/or interacts with at least one amino acid sequence selected from the group consisting of SEQ ID NO: 85 and SEQ ID NO: 86.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as *P. aeruginosa* infection. The subject may have a *P. aeruginosa* infection or is predisposed to developing a *P. aeruginosa* infection. Subjects "predisposed to developing a *P. aeruginosa* infection", or subjects "who may be at elevated risk for contracting a *P. aeruginosa* infection", are those subjects with a subject undergoing surgery, a subject being treated for a major illness, a trauma patient, an intravenous drug user, a subject having severe burns, a subject using a breathing machine, a subject with a catheter, a subject undergoing chemotherapy, a subject having diabetes, a subject with cystic fibrosis, a subject with tuberculosis, a subject with HIV, and a subject with a compromised immune system.

As used herein, the terms "treat", "treating" or "treatment" refer to therapeutic treatment, wherein the object is to clear or reduce the bacterial burden of an infectious agent in a subject that has been clinically diagnosed with an infection, such as pneumonia, bacteremia, peritonitis, sepsis, and/or an abscess. The terms include inhibition of progression of disease or of worsening of infection. The terms also include positive prognosis of disease, i.e., the subject may be free of infection or may have reduced or no bacterial titers upon administration of a therapeutic agent such as an antibody disclosed herein. "Treatment" can also mean prolonging survival as compared to expected survival if not receiving treatment. Those in need of treatment include those already with the infection as well as those prone to acquire the *P. aeruginosa* infection, e.g., in burn patients or immunosuppressed patients susceptible to bacterial infection, e.g., *P. aeruginosa* infection. The therapeutic agent may be administered at a therapeutic dose to the subject.

As used herein, the terms "prevent" or "mitigate" refer to prophylactic or preventative measures, wherein the object is to prevent or slow down (lessen) a *P. aeruginosa* infection, or symptom associated with the infection. Beneficial or desired clinical results include, but are not limited to, alleviation of symptoms, diminishment of extent of infection, stabilized (i.e., not worsening) state of disease, clearance or reduction of the infectious agent such as *P. aeruginosa* in a subject, a delay or slowing of disease progression, amelioration or palliation of the disease state, and remission (whether partial or total), whether detectable or undetectable.

As used herein, the terms "nosocomial disease" and "nosocomial infection" refer to a disease or infection originating in a hospital or other healthcare facility. Nosocomial infections can be caused by *P. aeruginosa*, e.g., *P. aeruginosa* resistant to antibiotics. In certain aspects, a nosocomial infection is not present or incubating prior to the subject being admitted to the hospital or healthcare facility, and is acquired or contracted after the subject's admittance to the hospital or healthcare facility.

GENERAL DESCRIPTION

As described above, the bacterial T3SS is an important virulence factor of Gram-negative bacteria, including *P. aeruginosa*. The PcrV protein, located at the end of the T3SS apparatus, forms a ring-type structure on the tip of the needle. The needle tip protein is accessible to antibodies as one of the two proteins present on the external surface of the bacteria.

As such, provided herein are antibodies, bispecific antigen binding molecules, and antigen-binding fragments thereof that bind *P. aeruginosa* PcrV. Antibodies that target PcrV can prevent injection of the bacterial toxins into an infected cell, leading to decreased inflammation, cell death, and dissemination of the bacteria. Antibodies that target PcrV can block pore-mediated membrane permeability in an infected host cell. These anti-PcrV antibodies, bispecific antigen-binding molecules, and antigen-binding fragments thereof are useful in treating and/or mitigating *P. aeruginosa* infection, treating and/or mitigating symptoms of *P. aeruginosa* infection, and preventing development of or progression of symptoms of *P. aeruginosa* infection. In some aspects, the anti-PcrV antibodies prevent development of or progression of *P. aeruginosa*-caused pneumonia.

Methods for treating patients with *P. aeruginosa* infection are provided herein. Methods for preventing development of or progression of symptoms of *P. aeruginosa* infection are provided herein. Methods for preventing signs of *P. aeruginosa*, such as a positive culture from blood, skin, urine, pus, or other body fluid samples or radiographic imaging suggestive of *P. aeruginosa* infection, or findings on physical exam suggestive of *P. aeruginosa* infection such as, but not limited to, skin or bone ulcers, or abnormal vital signs, are provided herein. In some aspects, the patient may have cystic fibrosis. In some aspects, the patient may be on a mechanical ventilator. In some aspects the patient is a neutropenic cancer patient. In some aspects, the patient is a burn victim. In some aspects, the patient suffers from tuberculosis.

In some embodiments the patient has an antibiotic-resistant *P. aeruginosa* infection. In some embodiments the patient has a co-infection such as a *S. aureus* infection, for example, an antibiotic-resistant *S. aureus* infection. In some embodiments both the *S. aureus* and the *P. aeruginosa* infections are antibiotic-resistant. In some embodiments the patient has a co-infection with a Gram-negative bacteria or a Gram-positive bacteria.

General Methods

Standard methods in molecular biology are described Sambrook, Fritsch and Maniatis (1982 & 1989 $2^{nd}$ Edition, 2001 $3^{rd}$ Edition) Molecular Cloning, A Laboratory Manual, Cold Spring Harbor Laboratory Press, Cold Spring Harbor, N.Y.; Sambrook and Russell (2001) Molecular Cloning, 3.sup.rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, N.Y.; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, N.Y., pp. 139-243; Carpenter, et aL (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272:10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, N.Y.; Kay et al. (1996) Phage Display of Peptides and Proteins: A Laboratory Manual, Academic Press, San Diego, Calif.; de Bruin et al. (1999) Nature Biotechnol. 17:397-399). Single chain antibodies and diabodies are described (see, e.g., Malecki et al. (2002) Proc. Natl. Acad. Sci. USA 99:213-218; Conrath et al. (2001) J. Biol. Chem. 276:7346-7350; Desmyter et al. (2001) J. Biol. Chem. 276:26285-26290; Hudson and Kortt (1999) J. Immunol. Methods 231:177-189; and U.S. Pat. No. 4,946,778). Bifunctional antibodies are provided (see, e.g., Mack, et al. (1995) Proc. Natl. Acad. Sci. USA 92:7021-7025; Carter (2001) J. Immunol. Methods 248:7-15; Volkel, et al. (2001) Protein Engineering 14:815-823; Segal, et al. (2001) J. Immunol. Methods 248:1-6; Brennan, et al. (1985) Science 229:81-83; Raso, et al. (1997) J. Biol. Chem. 272:27623; Morrison (1985) Science 229:1202-1207; Traunecker, et al. (1991) EMBO J. 10:3655-3659; and U.S. Pat. Nos. 5,932,448, 5,532,210, and 6,129,914). Fully human antibodies may also be developed in genetically engineered mice such as the VelociMouse. See e.g., DeChiara et al., Producing fully ES cell-derived mice from eight-cell stage embryo injections, Methods Enzymol, 476:285-94 (2010); Dechiara et al., VelociMouse: fully ES cell-derived FO-generation mice obtained from the injection of ES cells into eight-cell-stage embryos. Methods Mol Biol, 530:311-24 (2009); U.S. Pat. Nos. 7,576,259; 7,659,442; or 7294754, and US2008/0078000A1.

Purification of antigen is not typically necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) Immunity 7:283-290; Wright et al. (2000) Immunity 13:233-242; Preston et al., supra; Kaithamana et al. (1999) J. Immunol. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2.sup.nd ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

Anti-PcrV Antibodies

Passive immunotherapy for prophylaxis or treatment of infectious diseases has been used for more than a century, usually in the form of convalescent human sera that contains high titers of neutralizing antibodies (Good et al., 1991; Cancer 68: 1415-1421). Today, several purified monoclonal antibodies are currently in preclinical and clinical development for use as anti-microbials (Marasco et al 2007; Nature Biotechnology 25: 1421-1434). Certain antibodies have been described that bind to P. aeruginosa PcrV (See e.g. Francois et al., 2012; Crit. Care Med. 40: 2320-2326; and WO2009088032).

The inventors have described herein fully human antibodies and antigen-binding fragments thereof that specifically bind to P. aeruginosa PcrV and modulate the T3SS virulence mechanism. The anti-PcrV antibodies may bind to PcrV with high affinity. In certain embodiments, the antibodies may bind to PcrV and prevent or mitigate cell death. In certain embodiments, the antibodies may prevent the translocation of bacterial toxins into the host cell, and as such may inhibit or neutralize P. aeruginosa infection. In some embodiments, the antibodies may function by blocking T3SS pore-mediated membrane permeability in a host cell. In certain embodiments, the antibodies provided herein may mediate antibody dependent cell-mediated cytotoxicity (ADCC) and as such, may aid in destroying cells that harbor the bacteria. In certain embodiments, the antibodies may act in both fashions, e.g. they may neutralize bacterial infectivity and may mediate ADCC. In some aspects, the antibodies can decrease bacterial load, e.g. lung bacterial load, relative to similarly situated but untreated subjects or populations. In some aspects, the antibodies can increase survival or decrease mortality, relative to similarly situated but untreated subjects or populations. In some embodiments, the antibodies may be useful for treating a subject suffering from a P. aeruginosa infection. The antibodies when administered to a subject in need thereof may reduce the infection by P. aeruginosa in the subject. They may be used alone or as adjunct therapy with other therapeutic moieties or modalities known in the art for treating a bacterial infection. Furthermore, the identified antibodies can be used prophylactically (before infection) to protect a subject, e.g. a mammal, from infection, or can be used therapeutically (after infection is established) to ameliorate a previously established infection, or to ameliorate at least one symptom associated with the infection.

The full-length amino acid sequence of P. aeruginosa PcrV protein is shown in Gen Bank as accession number 250397.1 and also in SEQ ID NO: 77. A truncated PcrV protein (PcrV_136-257) is shown in SEQ ID NO: 79. Both proteins can be labeled with a 6-histidine tag: SEQ ID NO: 78 for the full length PcrV and SEQ ID NO: 80 for the truncated PcrV.

In certain embodiments, the antibodies provided herein are obtained from mice immunized with a primary immunogen, such as a full-length PcrV, or with a truncated version of the protein. The immunogen may be any immunogenic fragment of the PcrV protein or DNA encoding the active fragment thereof. The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-PcrV antibodies disclosed herein are able to bind to and neutralize the activity of P. aeruginosa, as determined by in vitro or in vivo assays. The ability of the antibodies of this disclosure to bind to and neutralize the activity of P. aeruginosa may be measured using any standard method known to those skilled in the art, including binding assays, or activity assays, as described herein.

Non-limiting, exemplary in vitro assays for measuring binding activity are illustrated in Example 3, herein. In Example 3, the binding affinity and dissociation constants of anti-PcrV antibodies for full length PcrV (6his labeled, SEQ ID NO: 78) or truncated PcrV (6his labeled, SEQ ID NO: 80) were determined by Biacore. In Examples 6 and 7, neutralization assays were used to determine the ability of the antibodies to neutralize two different strains of *P. aeruginosa*.

The antibodies specific for PcrV may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or an MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to *P. aeruginosa* PcrV. An antibody fragment may include a Fab fragment, a F(ab')2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$, (V) $V_H$-$C_H1$-$C_H2$-$C_H3$; (Vi) $V_H$-$C_H2$-$C_H3$; $V_H$—$C_L$; $V_L$—$C_H1$; (ix) $V_L$-$C_H2$; (X) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Preparation of Human Antibodies

Methods for generating human antibodies in transgenic mice are known in the art. Any such known methods can be used in the context of the present disclosure to make human antibodies that specifically bind to *P. aeruginosa* PcrV. An immunogen comprising any one of the following can be used to generate antibodies to PcrV. In certain embodiments, the antibodies of the disclosure are obtained from mice immunized with a full-length PcrV, for example, Gen Bank accession numbers NP_250397.1 (SEQ ID NO: 77) or a truncated PcrV protein, for example, PcrV_136-257 (SEQ ID NO: 79). Alternatively, the PcrV protein or a fragment thereof may be produced using standard biochemical techniques and modified and used as immunogen. In one embodiment, the immunogen is a recombinant PcrV protein or fragment thereof. In certain embodiments, the immunogen may be a commercially available PcrV protein. In certain embodiments, one or more booster injections may be administered. In certain embodiments, the booster injections may comprise one or more commercially available PcrV proteins. In certain embodiments, the immunogen may be a recombinant PcrV protein expressed in *E. coli* or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to PcrV are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody, for example wild-type or modified IgG1 or IgG4. While the constant region selected may vary according to specific use, high affinity antigen-binding and target specificity characteristics reside in the variable region.

Bioequivalents

The anti-PcrV antibodies and antibody fragments disclosed herein encompass proteins having amino acid sequences that vary from those of the described antibodies, but that retain the ability to bind PcrV. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment disclosed herein.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies disclosed herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-PcrV Antibodies Comprising Fc Variants

According to certain embodiments, anti-PcrV antibodies are provided comprising an Fc domain comprising one or more mutations that enhance or diminish antibody binding to the FcRn receptor, e.g., at acidic pH as compared to neutral pH. For example, the present disclosure includes anti-PcrV antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, provided herein are anti-PcrV antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., 1307A, E380A and N434A); and 433K and 434F (e.g., H433K and N434F). All possible combinations of the foregoing Fc domain mutations and other mutations within the antibody variable domains disclosed herein are contemplated within the scope of the present disclosure.

The present disclosure also includes anti-PcrV antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies provided herein comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013).

Biological Characteristics of the Antibodies

In general, the antibodies of the present disclosure function by binding to PcrV. For example, the present disclosure includes antibodies and antigen-binding fragments of antibodies that bind PcrV or PcrV_136-257 (e.g., at 25° C. or at 37° C.) with a $K_D$ of less than $10^{-7}$M, as measured by surface plasmon resonance, e.g., using the assay format as described herein. In certain embodiments, the antibodies or antigen-binding fragments thereof bind PcrV with a $K_D$ of less than about 10 nM, less than about 5 nM, less than about 1 nM, less than about 500 pM, less than 250 pM, or less than 100 pM, as measured by surface plasmon resonance, e.g., using the assay format as described herein, or a substantially similar assay.

The present disclosure also includes antibodies and antigen-binding fragments thereof that bind PcrV with a dissociative half-life (t½) of greater than about 10 minutes as measured by surface plasmon resonance at 25° C., or greater than about 1 minute as measured by surface plasmon resonance at 37° C. e.g., using an assay format as defined herein, or a substantially similar assay. In certain embodiments, the antibodies or antigen-binding fragments of the present disclosure bind PcrV with a t1/2 of greater than about 1 minute, of greater than about 10 minutes, of greater than about 30 minutes, of greater than about 60 minutes, of greater than about 100 minutes, of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., or at 37° C. e.g., using an assay format as defined herein (e.g., mAb-capture or antigen-capture format), or a substantially similar assay.

Also included herein are antibodies or antigen-binding fragments thereof that neutralize *P. aeruginosa* PcrV-mediated toxicity, for example, in A549 cells as shown in Example 6. In some embodiments, the antibodies exhibit a neutralization potency against *P. aeruginosa* strain 6077 with an $IC_{50}$ ranging from about $10^{-11}$ M to about $10^{-7}$ M. In some embodiments, the antibodies exhibit a neutralization potency against *P. aeruginosa* strain ATCC 700888 with an $IC_{50}$ ranging from about $10^{-9}$ M to about $10^{-7}$ M. The antibodies provided herein also neutralize *P. aeruginosa* PcrV-mediated RBC hemolysis as shown in Example 7. In some embodiments, the antibodies exhibit a neutralization potency against strain 6077 with an $IC_{50}$ ranging from about $10^{-10}$ M to about $10^{-7}$M. In some embodiments, the antibodies exhibit a neutralization potency against strain ATCC 700888 with an $IC_{50}$ ranging from about $10^{-10}$ M to about $10^{-8}$ M. Furthermore, the antibodies provided herein cross-compete with other antibodies that bind PcrV, as shown in Example 4.

Also included herein are antibodies that prevent individual mortality or decrease population mortality rates. In some embodiments, the antibodies can be administered prophylactically. In some embodiments, the antibodies can be administered therapeutically. In some embodiments, the antibodies, when dosed at 5 mg/kg, exhibit 100% improved survival in a mouse model of pneumonia, as shown in Example 8. In some embodiments, the antibodies exhibit improved survival even at lower dosages, for example, 1 mg/kg, or 0.2 mg/kg, or even 0.04 mg/kg, as shown in Example 9.

Also included herein are antibodies that decrease bacterial load, for example, lung bacterial load, in a subject or population. In some embodiments, the antibodies can be administered prophylactically. In some embodiments, the antibodies can be administered therapeutically. In some embodiments, the antibodies, when dosed at either 0.1 or 0.2 mg/kg, or at 25 mg/kg, demonstrate a decrease in bacterial load by 3 to 4 logs more than untreated subjects in a mouse model of pneumonia, as shown in Example 10 and Example 11.

In one embodiment, the antibodies provided herein can have one or more of the following characteristics: (a) comprise three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, and 50; and three light chain CDRs (LCDR1, LCDR2 and LCDR3) contained within any one of the light chain variable region (LCVR) sequences selected from the group consisting of SEQ ID NOs: 10, 26, 42, and 58; (a) comprise three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, and 50; and three light chain CDRs (LCDR1, LCDR2 and LCDR3) contained within any one of the light chain variable region (LCVR) sequences selected from the group consisting of SEQ ID NOs: 10, 26, 42, and 58; (b) are fully human monoclonal antibodies; (c) bind to full length PcrV with a dissociation constant ($K_D$) of less than $10^{-8}$M, as measured in a surface plasmon resonance assay at 25° C.; (d) bind to full length PcrV with a dissociation constant ($K_D$) of less than $10^{-8}$M, as measured in a surface plasmon resonance assay at 37° C.; (e) demonstrate neutralization of *P. aeruginosa* strain 6077 with an $IC_{50}$ ranging from about $10^{-11}$ M to about $10^{-8}$ M in a cytotoxicity assay; (f) demonstrate neutralization of *P. aeruginosa* strain ATCC 700888 with an $IC_{50}$ ranging from about $10^{-9}$ M to about $10^{-7}$M in a cytotoxicity assay; (g) demonstrate neutralization of *P. aeruginosa* strain 6077 with an $IC_{50}$ ranging from about $10^{-10}$M to about $10^{-6}$M in a hemolytic assay; (h) demonstrate neutralization of *P. aeruginosa* strain ATCC 700888 with an $IC_{50}$ ranging from about $10^{-10}$M to about $10^{-7}$M in a hemolytic assay; (i) decrease mortality from *P. aeruginosa* strain 6206 or strain 6077 in mice treated prophylactically with 5 mg/kg relative to untreated mice in an acute pneumonia model; (j) decrease mortality from *P. aeruginosa* strain 6206 or strain 6077 in mice treated prophylactically with 1.0, 0.2 or 0.04 mg/kg relative to untreated mice in an acute pneumonia model; (k) decrease lung bacterial burden of *P. aeruginosa* strain 6206 in mice treated prophylactically at 0.1 mg/kg or 0.2 mg/kg relative to untreated mice in an acute pneumonia model; (l) decrease lung bacterial burden of *P. aeruginosa* strain PA01 in mice treated prophylactically at 25 mg/kg relative to untreated mice in an acute pneumonia model; and/or (m) cross-compete with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

In a related embodiment, the antibodies or antigen-binding fragments thereof as provided herein can have one or more of the following characteristics: (n) bind to full length PcrV (SEQ ID NO: 77) with an $EC_{50}$ of less than about $10^{-8}$M; (o) bind to PcrV 136-233 (SEQ ID NO: 81) with an $EC_{50}$ of less than about $10^{-8}$M; (p) interact with at least one amino acid sequence selected from the group consisting of (i) amino acid residues ranging from about position 150 to about position 170 of SEQ ID NO: 78 and (ii) amino acid residues ranging from about position 155 to about 170 of SEQ ID NO: 78; and/or (q) interact with at least one amino acid sequence selected from the group consisting of SEQ ID NO: 85 and SEQ ID NO: 86.

The antibodies provided herein may possess one or more of the aforementioned biological characteristics, or any combinations thereof. Certain of the properties of the antibodies are summarized below. Other biological characteristics of the antibodies will be evident to a person of ordinary skill in the art from a review of the present disclosure including the working Examples herein.

Epitope Mapping and Related Technologies

Provided herein are anti-PcrV antibodies that interact with one or more amino acids found within the *P. aeruginosa* PcrV protein. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the PcrV protein (e.g. a linear epitope in a domain). Alternatively, the epitope may consist of a plurality of non-contiguous amino acids (or amino acid sequences) located within the PcrV protein (e.g. a conformational epitope). Illustratively, anti-PcrV antibodies or antigen-binding fragments thereof provided herein can bind to PcrV 136-233 (SEQ ID NO: 81); can interact with amino acid residues ranging from about position 150 to about position 170 of SEQ ID NO: 78; can interact with amino acid residues ranging from about position 155 to about 170 of SEQ ID NO: 78; and/or can interact with at least one amino acid sequence selected from the group consisting of SEQ ID NO: 85 and SEQ ID NO: 86.

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids and noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies into groups of antibodies binding different epitopes.

In certain embodiments, the anti-PcrV antibodies or antigen-binding fragments thereof bind an epitope within any one or more of the regions exemplified in PcrV protein, either in natural form, or recombinantly produced, or to a fragment thereof.

The present disclosure includes anti-PcrV antibodies that bind to the same epitope, or a portion of the epitope. Likewise, the present disclosure also includes anti-PcrV antibodies that compete for binding to the PcrV protein or a fragment thereof with any of the specific exemplary antibodies described herein. For example, the present disclosure includes anti-PcrV antibodies that cross-compete for binding to PcrV with one or more antibodies obtained from those antibodies described in Tables 1 and 2.

One can easily determine whether an antibody binds to the same epitope as, or competes for binding with, a reference anti-PcrV antibody by using routine methods known in the art. For example, to determine if a test antibody binds to the same epitope as a reference anti-PcrV antibody of the disclosure, the reference antibody is allowed to bind to the PcrV protein or peptide under saturating conditions. Next, the ability of a test antibody to bind to the PcrV protein is assessed. If the test antibody is able to bind to PcrV following saturation binding with the reference anti-PcrV antibody, it can be concluded that the test antibody binds to a different epitope than the reference anti-PcrV antibody. On the other hand, if the test antibody is not able to bind to the PcrV protein following saturation binding with the reference anti-PcrV antibody, then the test antibody may bind to the same epitope as the epitope bound by the reference anti-PcrV antibody provided herein.

To determine if an antibody competes for binding with a reference anti-PcrV antibody, the above-described binding methodology is performed in two orientations: In a first orientation, the reference antibody is allowed to bind to a PcrV protein under saturating conditions followed by assessment of binding of the test antibody to the PcrV protein. In a second orientation, the test antibody is allowed to bind to a PcrV protein under saturating conditions followed by assessment of binding of the reference antibody to the PcrV protein. If, in both orientations, only the first (saturating) antibody is capable of binding to the PcrV protein, then it is concluded that the test antibody and the reference antibody compete for binding to PcrV. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The disclosure provides a human anti-PcrV monoclonal antibody conjugated to a therapeutic moiety ("immunoconjugate"), such as an antibiotic to treat *P. aeruginosa* infection. As used herein, the term "immunoconjugate" refers to an antibody, which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to *P. aeruginosa*. In certain embodiments, the antibody may be conjugated to an agent specific for an infected cell. The type of therapeutic moiety that may be conjugated to the anti-PcrV antibody will take into account the condition to be treated and the desired therapeutic effect to be achieved. Examples of suitable agents for forming immunoconjugates are known in the art; see for example, WO 05/103081.

Multi-Specific Antibodies

The antibodies provided herein may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules provided herein, or variants thereof, may be constructed using standard molecular biological techniques (e.g., recombinant DNA and protein expression technology), as will be known to a person of ordinary skill in the art.

In some embodiments, *P. aeruginosa*-specific antibodies are generated in a bi-specific format (a "bi-specific") in which variable regions binding to distinct domains of *P. aeruginosa* PcrV are linked together to confer dual antigen specificity within a single binding molecule. Appropriately designed bi-specifics may enhance overall T3SS inhibitory efficacy through increasing both specificity and binding avidity. Variable regions with specificity for individual domains, or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L 1$) can be combined with two different $V_H$ domains (e.g., $V_H 1$ and $V_H 2$) to generate a bi-specific comprised of two binding "arms" ($V_H 1$-$V_L 1$ and $V_H 2$-$V_L 1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different anti-*P. aeruginosa* antibody, may be prepared in a bi-specific format using techniques described herein, or other techniques known to those skilled in the art. Antibody variable regions binding to distinct regions may be linked together with variable regions that bind to relevant sites on, for example, *P. aeruginosa*, to confer dual-antigen specificity within a single binding molecule. Appropriately designed bi-specifics of this nature serve a dual function. Variable regions with specificity for one *P. aeruginosa* antigen are combined with variable regions with specificity for PcrV and are paired on a structural scaffold that allows each variable region to bind to the separate antigens.

An exemplary bi-specific antibody format that can be used in the context of the present disclosure involves the use of a first immunoglobulin (Ig) $C_H 3$ domain and a second Ig $C_H 3$ domain, wherein the first and second Ig $C_H 3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H 3$ domain binds Protein A and the second Ig $C_H 3$ domain contains a mutation that reduces or abolishes Protein A binding such as an H95R modification (by IMGT exon numbering; H435R by EU numbering). The second $C_H 3$ may further comprise a Y96F modification (by IMGT; Y436F by EU). Further modifications that may be found within the second $C_H 3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab[2] bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The disclosure provides therapeutic compositions comprising the anti-PcrV antibodies or antigen-binding fragments thereof as provided herein. Therapeutic compositions in accordance with the present disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present disclosure is used for treating a disease or disorder in an adult patient, or for preventing such a disease, it is advantageous to administer the antibody normally at a single dose of about 0.01 to about 60 mg/kg body weight, for example, about 0.04 mg/kg, about 0.2 mg/kg, about 2.0 mg/kg, about 5 mg/kg, about 10 mg/kg, about 15 mg/kg, about 20 mg/kg, about 25 mg/kg, about 30 mg/kg, about 0.04 mg/kg to about 2.0 mg/kg, about 5 mg/kg to about 60 mg/kg, about 10 mg/kg to about 50 mg/kg, or about 20 mg/kg to about 50 mg/kg body weight. Depending on the severity of the condition, the frequency and the duration of the treatment can be adjusted. In certain embodiments, the antibody or antigen-binding fragment thereof can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 6 hours to 24 hours, at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition provided herein, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

Administration can be systemic or local. The pharmaceutical composition can be also delivered in a vesicle, in particular a liposome (see, for example, Langer (1990) Science 249: 1527-1533).

The use of nanoparticles to deliver the antibodies provided herein is also contemplated. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389). Nanoparticles may be developed and conjugated to antibodies contained in pharmaceutical compositions to target infected cells. Nanoparticles for drug delivery have also been described in, for example, U.S. Pat. No. 8,257,740, or U.S. Pat. No. 8,246,995.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present disclosure include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 1 to about 500 mg per dosage form in a unit dose; especially in the form of injection, it is preferred that the antibody is contained in about 1 mg to about 100 mg and in about 10 to about 250 mg for the other dosage forms.

Therapeutic Uses of the Antibodies

The antibodies provided herein are useful for the treatment, and/or prevention (e.g. prophylactic treatment) of a disease or disorder or condition associated with *P. aeruginosa* infection and/or for ameliorating at least one symptom associated with such disease, disorder or condition.

In certain embodiments, the antibodies disclosed herein are useful to treat subjects suffering from pneumonia, bacteremia, a bone infection, a joint infection, a skin infection, a burn infection, a wound infection, urinary tract infection, or any combination thereof, caused by *P. aeruginosa*. In one embodiment, an antibody or antigen-binding fragment thereof may be administered at a therapeutic dose to a patient with *P. aeruginosa* infection.

In some embodiments, provided herein are methods to ameliorate or reduce the severity, duration, or frequency of occurrence, of at least one symptom of a *P. aeruginosa* infection in a subject. For example, one or more anti-PcrV antibodies disclosed herein may be administered to relieve or prevent or decrease the severity of one or more of the symptoms or conditions of the disease or disorder. The antibodies may be used to ameliorate or reduce the severity of at least one symptom of *P. aeruginosa* infection including, but not limited to fever, chills, headache, fatigue, joint pain, stiffness, myalgia, diarrhea, vomiting, pain, itching, liquid discharge in the ears, rashes, pus-filled pimples on the skin, eye pain, redness in an eye, pneumonia, coughing, congestion, soft tissue discharge of green pus, sweet, fruity smell, and urinary tract infection.

It is also contemplated herein to administer one or more anti-PcrV antibodies disclosed herein prophylactically to subjects at risk for developing infection such as a subject undergoing surgery, a subject being treated for a major illness, a subject having severe burns, a subject using a breathing machine, a subject with a catheter, a subject undergoing chemotherapy, a subject having diabetes, a subject with cystic fibrosis, a subject with tuberculosis, a subject with HIV, or a subject with a compromised immune system.

Other subjects at risk for acquiring a *P. aeruginosa* infection include, for example, a person who is immunocompromised because of autoimmune disease, or those persons receiving immunosuppressive therapy (for example, following organ transplant), certain forms of anemia that deplete or destroy white blood cells, those persons receiving radiation or chemotherapy, or those persons afflicted with an inflammatory disorder.

It is also contemplated herein to administer one or more anti-PcrV antibodies in order to neutralize a *P. aeruginosa* infection. Exposing an individual or cells results in enhanced protection from cell death. In certain embodiments, the exposing may be in vitro or in vivo. The enhanced protection can be observed when the antibody is used alone, or when it is used in combination with one or more additional therapeutic agents or antibodies against *P. aeruginosa*.

It is also contemplated herein to administer one or more anti-PcrV antibodies in to decrease bacterial load in a subject. In some aspects, the one or more anti-PcrV antibodies or antigen-binding fragments thereof decrease bacterial load in a subject's lungs. The antibody or antigen-binding fragment thereof can block *P. aeruginosa* delivery of toxins into the host cell. In some aspects, treatment with an anti-PcrV antibody provided herein decreases *P. aeruginosa* bacterial load. In some aspects, treatment with an anti-PcrV antibody provided herein decreases bacterial load of *P. aeruginosa* and a co-infecting bacteria, for example, a Gram-negative or Gram-positive bacteria. In some aspects, treatment with an anti-PcrV antibody provided herein decreases *P. aeruginosa* bacterial load and *S. aureus* bacterial load.

In some embodiments, provided herein are methods of increasing the survival, or the likelihood of survival, of a subject suffering from infection with *P. aeruginosa*, or a subject at risk for *P. aeruginosa* infection.

One or more anti-PcrV antibodies can be administered to increase the survival, or the likelihood of survival, of a subject suffering from cystic fibrosis. In some aspects, the subject does not have pneumonia symptoms at the time of administration.

In a further embodiment, the present anti-PcrV antibodies are used for the preparation of a pharmaceutical composition for treating patients at risk for or suffering from a *P. aeruginosa* infection. In another embodiment, the present antibodies are used as adjunct therapy with any other agent or any other therapy known to those skilled in the art useful for treating or ameliorating a *P. aeruginosa* infection.

Combination Therapies

Combination therapies may include an anti-PcrV antibody as disclosed herein and any additional therapeutic agent that may be advantageously combined with such an antibody or a biologically active fragment thereof. The antibodies may be combined synergistically with one or more drugs or agents used to treat *P. aeruginosa* infection.

Exemplary agents for treating a bacterial infection may include, e.g., antibiotics, anti-inflammatory drugs (such as corticosteroids, and non-steroidal anti-inflammatory drugs), a different antibody to *P. aeruginosa*, or any other palliative therapy to treat a symptom of *P. aeruginosa* infection or for reducing the bacterial load in a patient. In certain embodiments, the second therapeutic agent may be an agent that helps to counteract or reduce any possible side effect(s) associated with an anti-PcrV antibody or antigen-binding fragment thereof, if such side effect(s) should occur.

Exemplary agents that may be advantageously combined with an anti-PcrV antibody include, without limitation, other agents that bind and/or inhibit *P. aeruginosa* activity (including other antibodies or antigen-binding fragments thereof, etc.) and/or agents which do not directly bind PcrV or another *P. aeruginosa* antigen but nonetheless inhibit bacterial activity including infectivity of host cells. In some aspects, the second therapeutic agent may be a therapeutic for treating infections associated with a different organism which may co-infect with *P. aeruginosa*, for example, a Gram-positive organism or a Gram-negative organism, e.g., an organism such as *S. aureus*. In some aspects, the additional therapeutic agent is a therapeutic useful for treating a co-infection. In some aspects, the additional therapeutic agent is useful for treating a *S. aureus* co-infection.

Exemplary antibiotics to combine with the anti-PcrV antibodies include: penicillins (piperacillin, piperacillin/tazobactam, mezlocillin, ticarcillin, ticarcillin/clavulanate), cephalosporins (ceftazidime, cefoperazone, cefepime), carbapenems (imipenem/cilastatin; meropenem), monobactams (aztreonam), aminoglycosides (tobramycin, gentamicin, amikacin), fluoroquinolones (ciprofloxacin, levofloxacin), and others (polymyxin B, colistin). Common treatment regimens include: for bacteremia: penicillin plus aminoglycoside; penicillin plus ciprofloxacin; cephalosporin, aztreonam or carbapenem plus aminoglycoside or ciprofloxacin; for CNS infection: ceftazidime, optionally plus an aminoglycoside; cefepime; ciprofloxacin; aztreonam; meropenem; for bone or joint infection: penicillin plus an aminoglycoside or ciprofloxacin; cephalosporin; aztreonam; fluoroquinolone; carbapenem; external otitis: cephalosporin; carbapenem; ciprofloxacin; cephalosporin plus aminoglycoside; keratinitis/corneal ulcer (eye): tobramycin (topical), optionally with piperacillin or ticarcillin (topical); ciprofloxacin or ofloxacin (topical); and urinary tract infection: ciprofloxacin; aminoglycoside; penicillin; cephalosporin; carbapenen. (See, e.g., Kasper, D. L, et al, eds: Harrison's Principles of Internal Medicine, 16th Ed., McGraw-Hill, 2005).

In one embodiment, the one or more additional therapeutic agents comprise one or more anti-PcrV antibodies. In certain embodiments, the second therapeutic agent is another different antibody, for example, another *P. aeruginosa* antibody, wherein the different antibody or antibodies may or may not bind PcrV or bind to the same epitope on PcrV, or an overlapping epitope. In certain embodiments, the second therapeutic agent is an antibody to a different *P. aeruginosa* antigen. In certain embodiments, the second therapeutic agent is an antibody to a different infectious bacteria, e.g. *S. aureus*. In some embodiments, non-competing antibodies may be combined and administered to a subject in need thereof. The antibodies comprising the combination may block the activity of the T3SS mechanism and/or inhibit some other activity of the bacteria.

As used herein, the term "in combination with" means that additional therapeutically active component(s) may be administered prior to, concurrent with, or after the administration of at least one anti-PcrV antibody provided herein. The term "in combination with" also includes sequential or concomitant administration of an anti-PcrV antibody and a second therapeutic agent.

The additional therapeutically active component(s) may be administered to a subject prior to administration of an anti-PcrV antibody. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PcrV antibody. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PcrV antibody. "Concurrent" administration, for purposes of the present disclosure, includes, e.g., administration of an anti-PcrV antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-PcrV antibody and the additional therapeutically active component may be administered intravenously, etc.); alternatively, each dosage form may be administered via a different route (e.g., the anti-PcrV antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-PcrV antibody "prior to", "concurrent with," or "after" (as those terms are defined herein above) administration of an additional therapeutically active component is considered administration of an anti-PcrV antibody "in combination with" an additional therapeutically active component.

The present disclosure includes pharmaceutical compositions in which an anti-PcrV antibody described herein is co-formulated with one or more of the additional therapeutically active component(s) as described elsewhere herein.

Administration Regimens

According to certain embodiments, a single dose of an anti-PcrV antibody of the disclosed herein (or a pharmaceutical composition comprising a combination of an anti-PcrV antibody and any of the additional therapeutically active agents mentioned herein) may be administered to a subject in need thereof. According to certain embodiments, multiple doses of an anti-PcrV antibody (or a pharmaceutical composition comprising a combination of an anti-PcrV antibody and any of the additional therapeutically active agents mentioned herein) may be administered to a subject over a defined time course. The methods according to this aspect of the disclosure comprise sequentially administering to a subject multiple doses of an anti-PcrV antibody described herein. As used herein, "sequentially administering" means that each dose of anti-PcrV antibody is administered to the subject at a different point in time, e.g., on different days separated by a predetermined interval (e.g., hours, days, weeks or months). The present disclosure includes methods which comprise sequentially administering to the patient a single initial dose of an anti-PcrV antibody, followed by one or more secondary doses of the anti-PcrV antibody, and optionally followed by one or more tertiary doses of the anti-PcrV antibody.

The terms "initial dose," "secondary doses," and "tertiary doses," refer to the temporal sequence of administration of the anti-PcrV antibody disclosed herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PcrV antibody, but generally may differ from one another in terms of frequency of administration. In certain embodiments, however, the amount of anti-PcrV antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-PcrV antibody, which is administered to a patient prior to the administration of the very next dose in the sequence with no intervening doses.

The methods may comprise administering to a patient any number of secondary and/or tertiary doses of an anti-PcrV antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments, the frequency at which the secondary and/or tertiary doses are administered to a patient can vary over the course of the treatment regimen. The frequency of administration may also be adjusted during the course of treatment by a physician depending on the needs of the individual patient following clinical examination.

Pharmaceutical Compositions

Provided herein pharmaceutical formulations comprising one or more anti-PcrV antibodies according to Table 1, and including, for example, or one or more (e.g., 1, 2, or 3) components thereof admixed with a pharmaceutically acceptable carrier or excipient. See, e.g., Remington's Pharmaceutical Sciences and U.S. Pharmacopeia: National Formulary, Mack Publishing Company, Easton, Pa. (1984). Methods for making such a pharmaceutical formulation comprising admixing a pharmaceutically acceptable carrier or excipient with the component(s) forms part of the present disclosure as do the pharmaceutical compositions that are produced by such methods.

The scope of the present disclosure includes desiccated, e.g., freeze-dried, anti-PcrV antibodies of the present disclosure, and a pharmaceutical composition thereof that includes a pharmaceutically acceptable carrier but substantially lacks water. In one embodiment, the pharmaceutical formulation is aqueous (includes water). In an embodiment of the disclosure, the pharmaceutical formulation is sterile.

Pharmaceutical formulations of therapeutic agents may be prepared by mixing with acceptable carriers, excipients, or stabilizers in the form of, e.g., lyophilized powders, slurries, aqueous solutions or suspensions (see, e.g., Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The mode of administration of pharmaceutical compositions comprising the anti-PcrV antibodies can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present disclosure provides methods for administering pharmaceutical formulations comprising an anti-PcrV antibody to a subject (e.g., a human) comprising introducing the formulation into the body of the subject, e.g., into a vein, the subcutis or the muscular tissue of the subject. For example, the method comprises piercing the body of the subject with a needle of a syringe and injecting the formulation into the body of the subject.

One or more vessels are provided herein (e.g., a plastic or glass vial, e.g., with a cap, or a chromatography column, hollow bore needle or a syringe cylinder) comprising an anti-PcrV antibody as disclosed herein or a pharmaceutical composition thereof comprising a pharmaceutically acceptable carrier. Methods for preparing one or more vessels comprising the composition are provided, the methods comprising introducing the components of the combination into one or more vessels, e.g., a single vessel comprising a combination of components which are co-formulated. In an embodiment of the present disclosure, the vessel(s) is/are then introduced into a kit.

Also provided is a device, e.g., an injection device, comprising an anti-PcrV antibody disclosed herein or a pharmaceutical composition thereof and methods of use thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an autoinjector, or filled at the point of use, e.g., by the user or a clinician) which, for example, includes a cylinder or barrel for holding fluid to be injected (e.g., comprising the antibody or fragment or a pharmaceutical composition thereof), a needle for piercing skin and/or blood vessels for injection of the fluid; and a plunger for pushing the fluid out of the cylinder and through the needle bore.

The pharmaceutical compositions disclosed herein may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556. Such needleless devices and methods of use thereof comprising the pharmaceutical composition are also part of the present disclosure.

Provided herein are methods for preparing one or more injection devices (e.g., pre-filled syringe or autoinjector) comprising an anti-PcrV antibody, the methods comprising introducing the components of the combination into one or more of such devices, e.g., a single device comprising the anti-PcrV antibody. In one embodiment, the injection device(s) is/are then introduced into a kit.

Also provided are kits comprising an anti-PcrV antibody. In one embodiment, the kit comprises the antibody in a vessel or injection device (e.g., pre-filled syringe or autoinjector). The kit can include a package insert including information concerning the pharmaceutical compositions and dosage forms in the kit. Generally, such information aids patients and physicians in using the enclosed pharmaceutical compositions effectively and safely. For example, any of the following information regarding antibodies provided herein may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Diagnostic Uses of the Antibodies

The anti-PcrV antibodies provided herein may be used to detect and/or measure *P. aeruginosa* in a sample, e.g., for diagnostic purposes. Some embodiments contemplate the use of one or more antibodies provided herein in assays to detect a disease or disorder such as *P. aeruginosa* infection. Exemplary diagnostic assays for *P. aeruginosa* may comprise, e.g., contacting a sample, obtained from a patient, with an anti-PcrV antibody of the disclosure, wherein the anti-PcrV antibody is labeled with a detectable label or reporter molecule or used as a capture ligand to selectively isolate *P. aeruginosa* from patient samples. Alternatively, an unlabeled anti-PcrV antibody can be used in diagnostic applications in combination with a secondary antibody which is itself detectably labeled. The detectable label or reporter molecule can be a radioisotope, such as 3H, 14C, 32P, 35S, or 125I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure *P. aeruginosa* in a sample include enzyme-linked immunosorbent assay (ELISA), radioimmunoassay (RIA), and fluorescence-activated cell sorting (FACS).

Samples that can be used in *P. aeruginosa* diagnostic assays according to the present disclosure include any tissue or fluid sample obtainable from a patient, which contains detectable quantities of either *P. aeruginosa*, or fragments thereof, under normal or pathological conditions. Generally, levels of *P. aeruginosa* in a particular sample obtained from a healthy patient (e.g., a patient not afflicted with a disease associated with *P. aeruginosa* will be measured to initially establish a baseline, or standard, level of *P. aeruginosa*. This baseline level of *P. aeruginosa* can then be compared against the levels of *P. aeruginosa* measured in samples obtained from individuals suspected of having a *P. aeruginosa*-associated condition, or symptoms associated with such condition.

The antibodies specific for *P. aeruginosa* may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-PcrV Antibodies

The DNA encoding full length PcrV or a truncated version of PcrV (PcrV 136-257) was cloned into target vectors for expression in *E. coli* BL21(DE3). The recombinant PcrV or truncated version of PcrV (PcrV 136-257) were purified from the supernatants of lysates from transformed *E. coli* cells. Human antibodies to PcrV were generated using full length PcrV.6×His (See also GenBank NP_250397.1; PAO1 strain; GenScript; See also SEQ ID NO: 77) or a truncated PcrV.6×His protein (See PcrV_136-257; GenScript, See also SEQ ID NO: 79). The immunogen was administered directly, with an adjuvant to stimulate the immune response, to a VELOCIMMUNE® mouse (i.e., an engineered mouse comprising DNA encoding human Immunoglobulin heavy and kappa light chain variable regions), e.g., as described in U.S. Pat. No. 8,502,018. The antibody immune response was monitored by a PcrV-specific immunoassay. When a desired immune response was achieved, anti-PcrV antibodies were isolated directly from antigen-positive B cells without fusion to myeloma cells, as described in U.S. Pat. No. 7,582,298, herein specifically incorporated by reference in its entirety. Using this method, several fully human anti-PcrV antibodies (i.e., antibodies possessing human variable domains and human constant domains) were obtained.

Exemplary antibodies generated according to the foregoing methods were designated as follows: H1H29329P, H1H29332P, H1H29336P, and H1H29339P.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected exemplary anti-PcrV antibodies of the invention. The corresponding nucleic acid sequence identifiers are set forth in Table 2. Table 3 provides sequence identifiers for full length heavy and light chain amino acid sequences.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H29329P | 2 | 4 | 6 | 8 | 10 | 12 | 14 | 16 |
| H1H29332P | 18 | 20 | 22 | 24 | 26 | 28 | 30 | 32 |
| H1H29336P | 34 | 36 | 38 | 40 | 42 | 44 | 46 | 48 |
| H1H29339P | 50 | 52 | 54 | 56 | 58 | 60 | 62 | 64 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H29329P | 1 | 3 | 5 | 7 | 9 | 11 | 13 | 15 |
| H1H29332P | 17 | 19 | 21 | 23 | 25 | 27 | 29 | 31 |
| H1H29336P | 33 | 35 | 37 | 39 | 41 | 43 | 45 | 47 |
| H1H29339P | 49 | 51 | 53 | 55 | 57 | 59 | 61 | 63 |

TABLE 3

Sequence Identifiers for full length heavy and light chain sequences

| | SEQ ID NOs: | |
|---|---|---|
| Antibody Designation | Full length Heavy Chain Amino Acid | Full length Light Chain Amino Acid |
| H1H29329P | 65 | 66 |
| H1H29332P | 67 | 68 |
| H1H29336P | 69 | 70 |
| H1H29339P | 71 | 72 |

Antibodies are typically referred to herein according to the following nomenclature: Fc prefix (e.g. "H4H"), followed by a numerical identifier (e.g. "13290," "13291," "13295," etc.), followed by a "P" suffix, as shown in Tables 1, 2, and 3. Thus, according to this nomenclature, an antibody may be referred to herein as, e.g., "H1H29329P," "H1H29332P," "H1H29336P," etc. The prefix on the antibody designations used herein indicate the particular Fc region isotype of the antibody. In particular, an "H1H" antibody has a human IgG1 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1-3—will remain the same, and the binding properties are expected to be identical or substantially similar regardless of the nature of the Fc domain.

Antibody Comparators

A first comparator antibody, REGN3514 (Control I, HC/LC SEQ ID NOs: 73/74) is an anti-PcrV antibody having sequences reported in WO 2013/070615. A second comparator antibody, REGN3977 (Control III, HC/LC SEQ ID NOs: 75/76) is an anti-PcrV antibody having sequences first reported in U.S. Pat. No. 7,494,653. A third comparator anti-PcrV antibody is REGN7070 (Control V, HC/LC SEQ ID NOs: 83/84). Isotype control antibodies REGN1932 and REGN684 (Controls II and IV, respectively) are used in the experiments below.

Example 3. Biacore Binding Affinities and Kinetic Constants of Human Monoclonal Anti-PcrV Antibodies The equilibrium dissociation constant ($K_D$) for different PcrV reagents binding to purified anti-PcrV monoclonal antibodies were determined using a real-time surface plasmon resonance based Biacore T200 biosensor. All binding studies were performed in 10 mM HEPES, 150 mM NaCl, 3.4 mM EDTA and 0.05% v/v Tween-20, pH 7.4 (HBS-EP) running buffer at 25° C. and 37° C. The Biacore CM5 sensor chip surface was first derivatized by amine coupling with the anti-human Fcγ specific polyclonal antibody (Jackson ImmunoResearch Cat. #109-005-098) to capture anti-PcrV monoclonal antibodies. Binding studies were performed on different concentrations of full-length PcrV.6xhis (SEQ ID NO: 78) and PcrV (aa136-257).6xhis (SEQ ID NO: 80) (90 nM-3.33 nM; 3-fold serial dilution) prepared in HBS-EP running buffer. Proteins were injected over the captured anti-PcrV monoclonal antibody surface for 4 minutes at a flow rate of 50 μL/minute, while the dissociation of monoclonal antibody bound PcrV reagent was monitored for 10 minutes in HBS-EP running buffer.

Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and } t\,1/2\,(\min) = \frac{\ln(2)}{60*kd}$$

Binding kinetic parameters for full-length PcrV.6xhis and PcrV (aa136-257).6xhis binding to the anti-PcrV monoclonal antibodies at 25° C. and 37° C. are shown in Tables 4 through 7.

TABLE 4

Binding Kinetics of Anti-PcrV mAbs to Full-length PcrV.6xhis at 25° C.

| mAb Captured | mAb Capture Level (RU) | 90 nM Ag Bound (RU) | $k_a$ (1/Ms) | $k_d$ (1/s) | $K_D$ (M) | t½ (min) |
|---|---|---|---|---|---|---|
| H1H29336P | 283.9 ± 2.2 | 102.1 | 4.90E+05 | ≤1.00E−05 | 2.04E−11 | ≥1155 |
| H1H29339P | 364.7 ± 4.5 | 140.4 | 3.65E+05 | ≤1.00E−05 | 2.74E−11 | ≥1155 |
| H1H29332P | 504.4 ± 2.8 | 151.9 | 2.37E+05 | 1.30E−05 | 5.48E−11 | 888.5 |
| H1H29329P | 438.4 ± 2.3 | 81 | 1.84E+05 | 9.50E−04 | 5.16E−09 | 12.2 |
| REGN3977 - Control III | 498.9 ± 2.5 | 146.4 | 2.07E+05 | 4.95E−04 | 2.39E−09 | 23.4 |
| REGN3514 - Control I | 618.6 ± 4.9 | 169.4 | 2.67E+05 | 3.90E−05 | 1.46E−10 | 296.2 |
| REGN1932 - Isotype Control II | 262.2 ± 0.4 | −5.9 | NB | NB | NB | NB |

TABLE 5

Binding Kinetics of Anti-PcrV mAbs to Full-length PcrV.6xhis at 37° C.

| mAb Captured | mAb Capture Level (RU) | 90 nM Ag Bound (RU) | $k_a$ (1/Ms) | $k_d$ (1/s) | $K_D$ (M) | $t\frac{1}{2}$ (min) |
|---|---|---|---|---|---|---|
| H1H29336P | 272.5 ± 1.4 | 80.7 | 8.60E+05 | ≤1.00E−05 | 1.16E−11 | ≥1155 |
| H1H29339P | 370.8 ± 4.4 | 129.6 | 5.08E+05 | ≤1.00E−05 | 1.97E−11 | ≥1155 |
| H1H29332P | 533.4 ± 2.1 | 163.2 | 2.93E+05 | 2.68E−05 | 9.20E−11 | 431.5 |
| H1H29329P | 430.7 ± 1.8 | 59.6 | 5.54E+05 | 5.05E−03 | 9.12E−09 | 2.3 |
| REGN3977 - Control III | 452.5 ± 3.0 | 135.7 | 2.63E+05 | 9.17E−04 | 3.48E−09 | 12.6 |
| REGN3514 - Control I | 517.6 ± 2.9 | 141.2 | 4.31E+05 | 1.96E−04 | 4.53E−10 | 59.1 |
| REGN1932 - Isotype Control II | 230.4 ± 0.5 | −22.5 | NB | NB | NB | NB |

TABLE 6

Binding Kinetics of Anti-PcrV mAbs to PcrV (aa136-257).6xhis at 25° C.

| mAb Captured | mAb Capture Level (RU) | 90 nM Ag Bound (RU) | $k_a$ (1/Ms) | $k_d$ (1/s) | $K_D$ (M) | $t\frac{1}{2}$ (min) |
|---|---|---|---|---|---|---|
| H1H29336P | 287.6 ± 1.5 | 48.2 | 3.67E+05 | 1.48E−05 | 4.08E−11 | 783.1 |
| H1H29339P | 370.9 ± 3.3 | 62.9 | 2.93E+05 | 2.76E−05 | 9.55E−11 | 418 |
| H1H29332P | 505.4 ± 1.2 | 68.5 | 1.33E+05 | 3.83E−05 | 2.85E−10 | 302 |
| H1H29329P | 431.6 ± 1.1 | 27.5 | 1.53E+05 | 2.30E−03 | 1.50E−08 | 5 |
| REGN3977 - Control III | 497.7 ± 2.6 | 66.6 | 2.23E+05 | 9.56E−04 | 4.28E−09 | 12.1 |
| REGN3514 - Control I | 614.9 ± 3.9 | 75.2 | 1.47E+05 | 1.22E−04 | 8.30E−10 | 94.7 |
| REGN1932 - Isotype Control II | 262.4 ± 0.3 | 0.4 | NB | NB | NB | NB |

TABLE 7

Binding Kinetics of Anti-PcrV mAbs to PcrV (aa136-257).6xhis at 37° C.

| mAb Captured | mAb Capture Level (RU) | 90 nM Ag Bound (RU) | $k_a$ (1/Ms) | $k_d$ (1/s) | $K_D$ (M) | $t\frac{1}{2}$ (min) |
|---|---|---|---|---|---|---|
| H1H29336P | 270.2 ± 0.7 | 40.1 | 5.44E+05 | 4.36E−05 | 8.09E−11 | 264.7 |
| H1H29339P | 364.9 ± 4.7 | 55.3 | 4.35E+05 | 8.15E−05 | 1.86E−10 | 141.8 |
| H1H29332P | 530.4 ± 1.9 | 69.4 | 1.78E+05 | 1.06E−04 | 5.95E−10 | 109.2 |
| H1H29329P | 421.7 ± 3.6 | 16.4 | 1.03E+05 | 1.10E−02 | 1.07E−07 | 1 |
| REGN3977 Control III | 445.8 ± 2.6 | 54.7 | 2.16E+05 | 2.45E−03 | 1.14E−08 | 4.7 |
| REGN3514 - Control I | 517.3 ± 1.7 | 60.7 | 2.46E+05 | 5.96E−04 | 2.42E−09 | 19.4 |
| REGN1932 - Isotype Control II | 229.0 ± 1.5 | −3 | NB | NB | NB | NB |

At 25° C., anti-PcrV monoclonal antibodies bound to full-length PcrV.6xhis (SEQ ID NO: 78) with $K_D$ values ranging from 20.4 pM to 5.16 nM, as shown in Table 4. At 37° C., anti-PcrV monoclonal antibodies bound to full-length PcrV.6xhis (SEQ ID NO: 78) with $K_D$ values ranging from 11.6 pM to 9.12 nM, as shown in Table 5. The isotype control antibody REGN1932 (Control II) exhibited no binding.

At 25° C., anti-PcrV monoclonal antibodies bound to PcrV (aa136-257).6xhis (SEQ ID NO: 80) with $K_D$ values ranging from 40.8 pM to 15.0 nM, as shown in Table 6. At 37° C., anti-PcrV monoclonal antibodies bound to PcrV (aa136-257).6xhis (SEQ ID NO: 80) with $K_D$ values ranging from 80.9 pM to 107 nM, as shown in Table 7. The isotype control antibody REGN1932 (Control II) exhibited no binding.

Example 4: Octet Cross-Competition Between Anti-PcrV Monoclonal Antibodies

Binding competition between a panel of anti-PcrV monoclonal antibodies was determined using a real-time, label-free bio-layer interferometry assay on an Octet® HTX biosensor (ForteBio, A Division of Pall Life Sciences). The entire experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at 1000 rpm. Octet biosensor tips (ForteBio Inc, #18-5122) coated with anti-Penta-his antibody were submerged for 90 seconds in wells containing 20 µg/mL solution of full-length PcrV with a C-terminal hexa-histidine tag (PcrV.6xhis; SEQ ID: 78) to capture ~0.62-0.74 nM PcrV.6xhis. The antigen captured biosensor tips were then saturated with anti-PcrV monoclonal antibody (subsequently referred to as mAb-1) by dipping into wells containing 50 µg/mL solution of mAb-1 for 5 minutes. To assess whether 2 antibodies compete for binding to their respective epitopes, the biosensor tips were subsequently dipped into wells containing 50 µg/mL solution of a second anti-PcrV monoclonal antibody (subsequently referred to as mAb-2) for 3 minutes. Biosensor tips were washed in HBS-EBT buffer between every step of the experiment. The real-time binding response was monitored over the entire course of the experiment and the binding response at the end of every step was recorded. The response of mAb-2 binding to full-length PcrV.6xhis pre-complexed with mAb-1 was compared and competitive/non-competitive behavior of different anti-PcrV monoclonal antibodies was determined as shown in Table 8.

TABLE 8

| Cross-Competition of Anti-PcrV Antibodies for Binding to Full-Length PcrV.6xhis. | |
|---|---|
| First mAb-1 Captured using AHC Octet Biosensors | mAb-2 Antibodies Shown to Compete with mAb-1 |
| H1H29339P | H1H29329P |
|  | H1H29332P |
|  | H1H29336P |
|  | REGN3514 |
| H1H29329P | H1H29339P |
|  | H1H29332P |
|  | H1H29336P |
|  | REGN3514 |
| H1H29332P | H1H29339P |
|  | H1H29329P |
|  | H1H29336P |
|  | REGN3514 |
| H1H29336P | H1H29339P |
|  | H1H29329P |
|  | H1H29332P |
|  | REGN3514 |
| REGN3514 - Control I | H1H29339P |
|  | H1H29329P |
|  | H1H29332P |
|  | H1H29336P |

Example 5: Binding of Human Monoclonal Antibodies to *P. aeruginosa* PcrV Recombinant Proteins by ELISA Anti-PcrV monoclonal antibodies (mAbs) were assessed by ELISA for their ability to bind to recombinant PcrV proteins. Nunc MicroSorp™ 96-well plates were coated with 0.2 µg per well of recombinant full-length *P. aeruginosa* PcrV (GenScript) (SEQ ID NO: 77) or a truncated form of the protein (encompassing amino acids 136 to 233 of the mature protein; GenScript) (SEQ ID NO: 81) and incubated overnight at 4° C. The following morning, plates were washed three times with wash buffer (Imidazole buffered saline with Tween-20) and blocked for 1.5 hours at 25° C. with 200 µl of blocking buffer (3% BSA in PBS). Plates were washed once and titrations of antibodies and isotype-matched control antibody (ranging from 33 nM-0.1 pM with 1:3 serial dilutions in 0.5% BSA/0.05% Tween-20/PBS) were added to the protein-containing wells and incubated for one hour at 25° C. Wells were washed three times and then incubated with 100 ng/ml anti-human HRP secondary antibody per well for one hour at 25° C. 100 µl of SuperSignal™ ELISA Pico Chemiluminescent Substrate was added to each well and signal was detected (Victor X3 plate reader, Perkin Elmer). Luminescence values were analyzed by a four-parameter logistic equation over a 10-point response curve (Graph Pad Prism).

As shown in Table 9, all anti-PcrV antibodies showed sub-nanomolar $EC_{50}$ binding to *P. aeruginosa* full length PcrV and sub-nanomolar $EC_{50}$ binding to truncated PcrV protein. Sub-nanomolar $EC_{50}$ binding of the anti-PcrV comparator antibody (Control I—REGN3514) was observed to both full length PcrV protein and the truncated PcrV protein, while the isotype control mAb (Control IV—REGN684) did not bind to either protein.

TABLE 9

Binding of anti-PcrV mAbs to *P. aeruginosa* PcrV proteins

| | Binding ($EC_{50}$) [M] | |
|---|---|---|
| mAb | Full length PcrV | PcrV 136-233 |
| H1H29329P | 5.969E-10 | 7.438E-09 |
| H1H29332P | 2.119E-09 | 8.139E-10 |
| H1H29336P | 2.276E-09 | 1.027E-09 |
| H1H29339P | 1.961E-09 | 8.562E-10 |
| Control I - REGN3514 | 6.957E-10 | 7.587E-09 |
| Control IV - Isotype Control | no binding | no binding |

Example 6: Ability of *P. aeruginosa* Anti-PcrV Monoclonal Antibodies to Neutralize PcrV-Mediated Cytotoxicity Anti-PcrV monoclonal antibodies were assessed for their ability to prevent PcrV-mediated lysis of A549 cells, a human lung epithelial cell line. A549 cells were seeded at a density of approximately $4.8 \times 10^5$ cells/ml in Ham's F-12K (supplemented with 10% heat-inactivated FBS and L-glutamine) into 96-well clear bottom-black tissue culture treated plates and incubated overnight at 37° C. with 5% $CO_2$. The next day, media was removed from the cells and replaced with 100 µl assay medium (DMEM without phenol red, supplemented with 10% heat-inactivated FBS). Titrations of purified antibodies or isotype-matched control (ranging from 33.3 pM-1.33 µM) were added in 50 µl and cells were incubated for 45 minutes at 37° C. with 5% $CO_2$.

Meanwhile, log phase cultures of *P. aeruginosa* strains 6077 (Gerald Pier, Brigham and Women's Hospital, Harvard University) and ATCC 700888 (ATCC) were prepared as follows: overnight *P. aeruginosa* cultures were grown in LB, diluted 1:50 in fresh LB and grown to $OD_{600}=~1$ at 37° C. with shaking. Cultures were washed once with PBS and diluted to $OD_{600}=0.03$ in PBS for both *P. aeruginosa* strains. Bacteria in 50 µl were added to the wells containing cells and antibody, incubated for two hours at 37° C. with 5% $CO_2$. Cell death was determined using the CytoTox-Glo™ Assay kit (Promega). Luminescence was detected using a plate reader (Victor, Perkin Elmer) and luminescence values were analyzed by a four-parameter logistic equation (Graph-Pad Prism).

As shown in Table 10, anti-PcrV mAbs (H1H29329P, H1H29332P, H1H29336P and H1H29339P) showed efficacy in preventing A549 cell death. All four monoclonal antibodies protected against both *P. aeruginosa* strains. Control anti-PcrV mAb (Control I—REGN3514) also demonstrated efficacy against both bacterial strains and the isotype control mAb (Control II) had no effect.

TABLE 10

Neutralization of *P. aeruginosa* PcrV-mediated Toxicity in an A549 Cytotoxicity Assay

| mAb | A549 Cytotoxicity Assay (IC50) [M] | |
| --- | --- | --- |
| | *P. aeruginosa* strain 6077 | *P. aeruginosa* strain ATCC 700888 |
| H1H29329P | 1.079E−08 | 5.428E−08 |
| H1H29332P | 6.474E−09 | 3.288E−08 |
| H1H29336P | 8.400E−10 | 6.372E−09 |
| H1H29339P | 3.329E−11 | 7.818E−09 |
| Control I - REGN3514 | 8.070E−10 | 1.784E−08 |
| Control II - Isotype Control | no efficacy | no efficacy |

Example 7: Ability of *P. aeruginosa* Anti-PcrV Monoclonal Antibodies to Neutralize PcrV-Mediated Cytotoxicity Anti-PcrV monoclonal antibodies were assessed for their ability to prevent PcrV-mediated lysis of rabbit red blood cells (rRBCs; Colorado Serum Co.).

Overnight cultures of *P. aeruginosa* strain 6077 and strain ATCC 700888 were grown in LB, diluted 1:50 in fresh LB and grown to $OD_{600}$=~1 at 37° C. with shaking. The culture was washed once with PBS and diluted to $OD_{600}$=0.15 in PBS for both *P. aeruginosa* strains. rRBCs were prepared by centrifuging a 50% rRBC suspension at 4° C. for 10 minutes at 2000 xg, replacing the supernatant with PBS, gently mixing the rRBC and PBS, and diluting the rRBC to 5%. In 96 well round-bottom plates, 10 μl of *P. aeruginosa* strain 6077 or ATCC 700888 were mixed with titrations of purified antibodies or isotype-matched control (ranging from 33.3 pM-1.33 μM) or Triton X-100 (lysis positive control) in 50 μl, followed by the addition of 50 μl 5% rRBC. Plates were incubated at 37° C. for two hours, with shaking at 550 rpm. At the end of the incubation period, plates were centrifuged at 25° C. for one minute at 200 xg, 75 μl of the supernatant was transferred to a flat clear bottom plate and absorbance ($A_{405}$) was detected using a plate reader (Victor X3, Perkin Elmer), and absorbance values were analyzed by a four-parameter logistic equation (GraphPad Prism).

As shown in Table 11, all four anti-PcrV mAbs showed efficacy in preventing rRBC hemolysis and protected against both *P. aeruginosa* strains. Control anti-PcrV mAb (Control I—REGN3514) also demonstrated efficacy against both bacterial strains and the isotype control mAb (Control IV—REGN684) had no effect.

TABLE 11

Neutralization of *P. aeruginosa* PcrV in Rabbit RBC Hemolysis Assay

| mAb | Rabbit RBC Hemolysis Assay ($IC_{50}$) [M] | |
| --- | --- | --- |
| | *P. aeruginosa* strain 6077 | *P. aeruginosa* strain ATCC 700888 |
| H1H29329P | 5.640E−08 | 2.389E−09 |
| H1H29332P | 1.525E−08 | 4.062E−09 |

TABLE 11-continued

Neutralization of *P. aeruginosa* PcrV in Rabbit RBC Hemolysis Assay

| mAb | Rabbit RBC Hemolysis Assay ($IC_{50}$) [M] | |
| --- | --- | --- |
| | *P. aeruginosa* strain 6077 | *P. aeruginosa* strain ATCC 700888 |
| H1H29336P | 2.051E−10 | 8.097E−10 |
| H1H29339P | 2.302E−09 | 5.586E−09 |
| Control I - REGN3514 | 2.441E−09 | 1.011E−09 |
| Control IV - Isotype Control | no efficacy | no efficacy |

Example 8: Efficacy of Anti-PcrV Monoclonal Antibodies in an In Vivo Model of Acute Pneumonia Anti-PcrV monoclonal antibodies (mAbs) that prevented PcrV-mediated toxicity in either the rabbit red blood cell (RBC) hemolysis assay (Example 7) or the A549 cytotoxicity assay (Example 6) were assessed for their ability to prevent mortality in a murine acute pneumonia model. Female BALB/c-ELITE mice (Charles River; 7-8 weeks old; n=5 per group) were injected subcutaneously with a single dose of 5 mg/kg of the purified antibodies or isotype-matched control. Two days post-injection of the mAbs, mice were challenged intranasally with 20 μl of either *P. aeruginosa* strain 6077 (at ~4.2×$10^6$ CFU/mouse) or strain 6206 (at ~1.2×$10^6$ CFU/mouse) that had been grown to log phase ($OD_{600}$=1) in TSB at 37° C., washed once and resuspended in PBS. The mice were monitored for survival for a total of seven days post-infection.

As shown in Table 12, all four anti-PcrV mAbs, H1H29329P, H1H29332P, H1H29336P and H1H29339P, prevented death of mice in an acute pneumonia model when administered at 5 mg/kg prophylactically against both *P. aeruginosa* strains. Control anti-PcrV mAb (Control I—REGN3514) also demonstrated efficacy against both bacterial strains. The isotype control mAb (Control IV—REGN684) had no protective effect.

TABLE 12

Prophylactic Treatment with Anti-PcrV mAbs in an Acute Pneumonia Model

| mAb | % Survival (Day 7 post-infection) | |
| --- | --- | --- |
| | *P. aeruginosa* strain 6077 | *P. aeruginosa* strain 6206 |
| H1H29329P | 100 | 100 |
| H1H29332P | 100 | 100 |
| H1H29336P | 100 | 100 |
| H1H29339P | 100 | 100 |
| Control I - REGN3514 | 100 | 100 |
| Control IV - REGN684 | 0 | 0 |

Example 9: In Vivo Efficacy of Anti-PcrV Monoclonal Antibodies in an Acute Pneumonia Model Using *P. aeruginosa* Strains 6077 and 6206

Anti-PcrV monoclonal antibodies (mAbs) that demonstrated efficacy in a murine acute pneumonia model when administered prophylactically at 5 mg/kg (H1H29329P, H1H29332P, H1H29336P, H1H29339P) were tested at lower doses to assess their ability to prevent mortality in a murine acute pneumonia model. Female BALB/c-ELITE mice (Charles River; 7-8 weeks old; n=5-10 per group) were injected subcutaneously with a single dose of either 1.0, 0.2 or 0.04 mg/kg of the purified antibodies or isotype-matched control. Two days post-injection of the mAbs, mice were challenged intranasally with 20 µl of *P. aeruginosa* strain 6077 (at ~4.5×10$^5$ CFU/mouse) or 6206 (at ~9×10$^5$ CFU/mouse) that had been grown to log phase (OD$_{600}$=1) in TSB at 37° C., washed once and resuspended in PBS. The mice were monitored for survival for a total of seven days post-infection.

As shown in Table 13, anti-PcrV mAbs H1H29336P and H1H29339P decreased mortality of mice when administered prophylactically at doses as low as 0.04 mg/kg against *P. aeruginosa* strain 6077 and as low as 0.2 mg/kg against *P. aeruginosa* strain 6206. In contrast, anti-PcrV mAbs H1H29329P and H1H29332P were unable to prevent mortality when tested at doses less than 1.0 mg/kg using the more cytotoxic strain 6206. Control anti-PcrV mAb (Control I—RENG3514) lost efficacy against *P. aeruginosa* strain 6077 and strain 6206 at doses less than 0.2 mg/kg and 1.0 mg/kg, respectively. Isotype control mAb (Control IV—REGN684) had no protective effect.

TABLE 13

Prophylactic Teatment with Anti-PcrV mAbs in an Acute Pneumonia Mouse Model

| mAb | mAb dose (mg/kg) | % Survival (Day 7 post-infection) *P. aeruginosa* strain 6077 | *P. aeruginosa* strain 6206 |
|---|---|---|---|
| H1H29329P | 1 | 100 | 80 |
|  | 0.2 | n.d. | 0 |
|  | 0.04 | n.d. | n.d. |
| H1H29332P | 1 | 100 | 80 |
|  | 0.2 | n.d. | 0 |
|  | 0.04 | n.d. | n.d. |
| H1H29336P | 1 | 100 | 80 |
|  | 0.2 | 100 | 80 |
|  | 0.04 | 70 | 0 |
| H1H29339P | 1 | 100 | 80 |
|  | 0.2 | 100 | 90 |
|  | 0.04 | 60 | 0 |
| REGN3514 - Control I | 1 | 100 | 40 |
|  | 0.2 | 80 | 0 |
|  | 0.04 | 0 | 0 |
| Control IV - Isotype Control | 1 | 20 | 0 |
|  | 0.2 | 0 | 0 |
|  | 0.04 | n.d. | n.d. | n.d.: no data (experiment not done)

Example 10: In Vivo Efficacy of Prophylactic Treatment with Anti-PcrV Monoclonal Antibodies in an Acute Pneumonia Model Using *P. aeruginosa* Strain 6206

This Example demonstrated the ability of prophylactically administered anti-PcrV monoclonal antibody to decrease bacterial burden in the lungs in a murine acute pneumonia model using *P. aeruginosa* strain 6206.

The H1H29339P anti-PcrV antibody prevented mortality in a murine acute pneumonia model when administered prophylactically, as shown in Example 9. In this experiment, the antibody was tested at low doses for its ability to decrease the bacterial burden in the lungs of mice using the same acute pneumonia model. Female BALB/c-ELITE mice (Charles River; 7-8 weeks old; n=5 per group) were subcutaneously injected with a single dose of either 0.1 or 0.2 mg/kg of the purified antibody or 0.2 mg/kg of isotype-matched control. Two days post-injection of the antibody, mice were challenged intranasally with 20 µl of *P. aeruginosa* strain 6206 (at ~1.2×10$^6$ CFU/mouse) that had been grown to log phase (OD$_{600}$=1) in TSB at 37° C., washed once and resuspended in PBS. The mice were sacrificed 16-18 hours post-infection, lungs were harvested and lung homogenates were plated for bacterial enumeration on LB agar plates.

As shown in Table 14, the anti-PcrV mAb H1H29339P decreased the bacterial burden in the lungs of mice infected with *P. aeruginosa* 6206 one log more than control anti-PcrV mAb (Control V—REGN7070) when administered at either 0.1 or 0.2 mg/kg and 3-4 logs more than the no antibody or isotype control mAb (Control IV) groups.

TABLE 14

Bacterial burden in the lungs of mice administered 0.1 or 0.2 mg/kg anti-PcrV mAb prophylactically in an acute pneumonia model using *P. aeruginosa* strain 6206

| mAb | mAb dose (mg/kg) | *P. aeruginosa* 6206 in lungs (CFU/g lungs) |
|---|---|---|
| H1H29339P | 0.1 | 3.23e6 |
|  | 0.2 | 1.10e5 |
| Control V - REGN7070 | 0.1 | 2.03e7 |
|  | 0.2 | 2.22e6 |
| Control IV - Isotype Control | 0.2 | 1.21e9 |
| No mAb | n.a. | 1.33e9 | n.a., not applicable

Example 11: In Vivo Efficacy of Prophylactic Treatment with Anti-PcrV Monoclonal Antibodies in an Acute Pneumonia Model Using *P. aeruginosa* Strain PAO1

This Example demonstrated the ability of prophylactically administered anti-PcrV monoclonal antibody to decrease bacterial burden in the lungs in a murine acute pneumonia model using *P. aeruginosa* strain PAO1, the most commonly used strain for research and, relative to more recently isolated *P. aeruginosa* strains, less cytotoxic.

The H1H29336P anti-PcrV antibody demonstrated efficacy in a murine acute pneumonia model when administered prophylactically against *P. aeruginosa* cytotoxic strains 6077 and 6206, as shown in Examples 8 through 10. Here, the antibody was tested against a noncytotoxic strain, PAO1. Female BALB/c-ELITE mice (Charles River; 7-8 weeks old; n=10 per group) were subcutaneously injected with a single dose of 25 mg/kg of purified antibodies or isotype-matched control. Two days post-injection of the mAb, mice were challenged intranasally with 20 µl of *P. aeruginosa* strain PAO1 (at 1×10$^8$ CFU/mouse) that had been grown to log phase (OD$_{600}$=1) in TSB at 37° C., washed once and resuspended in PBS. The mice were sacrificed 16-18 hours post-infection, lungs were harvested and lung homogenates were plated for bacterial enumeration on LB agar plates.

As shown in Table 15, anti-PcrV mAb H1H29336P decreased the bacterial burden in the lungs of mice infected with noncytotoxic *P. aeruginosa* strain PAO1 approximately 2 logs more than control anti-PcrV mAb (Control V—REGN7070) and 4 logs more than the no antibody or isotype control mAb (Control IV) groups.

TABLE 15

Bacterial burden in the lungs of mice administered 25 mg/kg anti-PcrV mAb prophylactically in an acute pneumonia model using *P. aeruginosa* strain PAO1

| mAb | mAb dose (mg/kg) | *P. aeruginosa* PAO1 in lungs (CFU/g lungs) |
|---|---|---|
| H1H29336P | 25 | 5.11e7 |
| Control V - REGN7070 | 25 | 1.24e9 |
| Control IV - Isotype Control | 25 | 9.34e11 |
| No mAb | n.a. | 2.34e11 | n.a., not applicable

Example 12: Anti-PcrV Antibody Epitope Binding by HDX-MS

Hydrogen-Deuterium Exchange Mass Spectrometry (HDX-MS) was performed to determine the amino acid residues of the *Pseudomonas aeruginosa* PcrV (SEQ ID NO: 78) interacting with H1H29336P and H1H29339P antibodies. A general description of the HDX-MS method is provided in e.g., Ehring (1999) *Analytical Biochemistry* 267(2):252-259; and Engen and Smith (2001) *Anal. Chem.* 73:256A-265A.

The HDX-MS experiments were performed on an integrated HDX-MS platform, consisting of a Leaptec HDX PAL system for the deuterium labeling and quenching, a Waters Acquity M-Class (Auxiliary solvent manager) for the sample digestion and loading, a Waters Acquity M-Class (pBinary solvent manager) for the analytical gradient, and a Thermo Q Exactive HF mass spectrometer for peptide mass measurement.

The labeling solution was prepared as PBS buffer in $D_2O$ at pD 7.0 (10 mM phosphate buffer, 140 mM NaCl, and 3 mM KCl, equivalent to pH 7.4 at 25° C.). For deuterium labeling, 10 μl of PcrV (from GenScript, 57.3 μM) or PcrV premixed with H1H29336P in 1:0.6 molar ratio (antigen to antibody complex) and 10 μl of PcrV (from GenScript, 31.7 μM) or PcrV premixed with H1H29339P in 1:0.6 molar ratio (antigen to antibody complex) were incubated at 20° C. with 90 μL of $D_2O$ labeling solution for various time-points in duplicates (e.g., non-deuterated control=0 second; deuterium-labeled for 5 minutes and 10 minutes). The deuteration reaction was quenched by adding 100 μl of quench buffer (0.5 M TCEP-HCl, 8 M urea and 1% formic acid) to each sample for a 5-minute incubation at 20° C. The quenched samples were then injected into a Waters HDX Manager for online pepsin/protease XIII digestion. The digested peptides were separated by a C8 column (1.0 mm×50 mm, NovaBioassays) at −9.5° C. with a 22-minute gradient from 0%-90% B (mobile phase A: 0.5% formic acid and 4.5% acetonitrile in water, mobile phase B: 0.5% formic acid in acetonitrile). The eluted peptides were analyzed by a Thermo Q Exactive HF mass spectrometry in LC-MS/MS or LC-MS mode.

The LC-MS/MS data of undeuterated PcrV sample were searched against a database including PcrV sequence and its reversed sequence using Byonic search engine (Protein Metrics). The search parameters were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D).

Deuterium Uptake (*D*-uptake) =

Average Mass (deuterated) − Average Mass (undeuterated)

Percentage of deuterium uptake (% *D*) =

$$\frac{D\text{-uptake for peptide at each time point} \times 100\%}{\text{Maximum } D\text{-uptake of the peptide}}$$

A total of 127 peptides from PcrV were identified from both PcrV alone and PcrV in complex with H1H29336P samples, representing 95% sequence coverage of PcrV. Any peptide which exhibited a differential percent D-uptake value above 5% was defined as significantly protected. Peptides corresponding to amino acids 155-170 (ALSAKQGIRIDAGGID SEQ ID NO: 85) on PcrV were significantly protected by H1H29336P (PcrV residues are numbered according to PcrV amino acid sequence of SEQ ID NO: 78). See Table 16.

A total of 133 peptides from PcrV were identified from both PcrV alone and PcrV in complex with H1H29339P samples, representing 98% sequence coverage of PcrV. Any peptide which exhibited a differential percent D-uptake value above 5% was defined as significantly protected. Peptides corresponding to amino acids 150-170 (SQINAALSAKQGIRIDAGGID—SEQ ID NO: 86) on PcrV were significantly protected by H1H29339P (PcrV residues are numbered according to PcrV amino acid sequence of SEQ ID NO: 78). See Table 17.

TABLE 16

PcrV peptides with significant protection upon formation of PcrV- H1H29336P complex compared to PcrV alone

| | | 5 min | | | 10 min | | | |
|---|---|---|---|---|---|---|---|---|
| | | PcrV-H1H29336P | PcrV | | PcrV-H1H29336P | PcrV | | |
| PcrV Residues | Charge (+) | Centroid MH⁺ | Centroid MH⁺ | Δ D | Centroid MH⁺ | Centroid MH⁺ | Δ D | Δ % D |
| 155-165 | 2 | 1173.10 | 1173.74 | −0.64 | 1172.99 | 1173.80 | −0.81 | −9.0 |
| 155-170 | 2 | 1587.45 | 1588.32 | −0.87 | 1587.37 | 1588.34 | −0.97 | −7.3 |

TABLE 16-continued

PcrV peptides with significant protection upon formation of PcrV-H1H29336P complex compared to PcrV alone

| PcrV Residues | Charge (+) | 5 min | | | 10 min | | | |
|---|---|---|---|---|---|---|---|---|
| | | PcrV-H1H29336P Centroid MH$^+$ | PcrV Centroid MH$^+$ | Δ D | PcrV-H1H29336P Centroid MH$^+$ | PcrV Centroid MH$^+$ | Δ D | Δ % D |
| 155-170 | 3 | 1587.59 | 1588.30 | −0.70 | 1587.50 | 1588.29 | −0.79 | −5.9 |
| 157-165 | 2 | 988.46 | 988.91 | −0.45 | 988.35 | 988.91 | −0.55 | −8.0 |
| 157-170 | 3 | 1402.70 | 1403.25 | −0.55 | 1402.61 | 1403.22 | −0.61 | −5.4 |
| 157-170 | 2 | 1402.78 | 1403.33 | −0.55 | 1402.68 | 1403.25 | −0.57 | −5.2 |
| 161-165 | 1 | 573.12 | 573.29 | −0.17 | 573.08 | 573.28 | −0.20 | −6.8 |
| 161-170 | 2 | 987.44 | 987.80 | −0.36 | 987.38 | 987.75 | −0.37 | −5.1 |

TABLE 17

PcrV peptides with significant protection upon formation of PcrV-H1H29339P complex compared to PcrV alone

| PcrV Residues | Charge (+) | 5 min | | | 10 min | | | |
|---|---|---|---|---|---|---|---|---|
| | | PcrV-H1H29339P Centroid MH$^+$ | PcrV Centroid MH$^+$ | Δ D | PcrV-H1H29339P Centroid MH$^+$ | PcrV Centroid MH$^+$ | Δ D | Δ % D |
| 150-156 | 1 | 716.24 | 716.46 | −0.22 | 716.23 | 716.63 | −0.40 | −6.8 |
| 155-165 | 2 | 1172.94 | 1173.78 | −0.84 | 1172.84 | 1173.91 | −1.07 | −11.8 |
| 155-170 | 2 | 1587.22 | 1588.29 | −1.07 | 1587.11 | 1588.49 | −1.38 | −9.7 |
| 157-165 | 2 | 988.35 | 988.85 | −0.50 | 988.25 | 988.95 | −0.70 | −9.5 |
| 157-168 | 2 | 1173.96 | 1174.55 | −0.59 | 1173.81 | 1174.68 | −0.87 | −8.1 |
| 157-170 | 2 | 1402.67 | 1403.30 | −0.63 | 1402.46 | 1403.43 | −0.97 | −7.4 |
| 161-165 | 1 | 573.07 | 573.28 | −0.21 | 573.06 | 573.30 | −0.24 | −8.3 |
| 161-170 | 2 | 987.31 | 987.71 | −0.40 | 987.17 | 987.79 | −0.62 | −7.1 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. An isolated recombinant antibody or antigen-binding fragment thereof that specifically binds to *P. aeruginosa* PcrV, wherein the antibody or antigen-binding fragment thereof comprises:
   (a) three heavy chain complementarity determining regions (CDRs) (HCDR1, HCDR2 and HCDR3) contained within a heavy chain variable region (HCVR) amino acid sequence of SEQ ID NO: 34; and three light chain CDRs (LCDR1, LCDR2 and LCDR3) contained within a light chain variable region (LCVR) amino acid sequence of SEQ ID NO: 42;
   (b) three HCDRs (HCDR1, HCDR2 and HCDR3) contained within an HCVR amino acid sequence of SEQ ID NO: 50; and three light chain LCDRs (LCDR1, LCDR2 and LCDR3) contained within an LCVR amino acid sequence of SEQ ID NO: 58;
   (c) three HCDRs (HCDR1, HCDR2 and HCDR3) contained within an HCVR amino acid sequence of SEQ ID NO: 2; and three light chain LCDRs (LCDR1, LCDR2 and LCDR3) contained within an LCVR amino acid sequence of SEQ ID NO: 10; or (d) three HCDRs (HCDR1, HCDR2 and HCDR3) contained within an HCVR amino acid sequence of SEQ ID NO: 18; and three light chain LCDRs (LCDR1, LCDR2 and LCDR3) contained within an LCVR amino acid sequence of SEQ ID NO: 26.

2. The isolated antibody or antigen-binding fragment thereof of claim 1, which is a fully human monoclonal antibody.

3. The isolated antibody or antigen-binding fragment thereof of claim 1, comprising an HCVR having an amino acid sequence of SEQ ID NO: 34 and an LCVR having an amino acid sequence of SEQ ID NO: 42.

4. The isolated antibody or antigen-binding fragment thereof of claim 1, comprising an HCVR having an amino acid sequence of SEQ ID NO: 50 and an LCVR having an amino acid sequence of SEQ ID NO: 58.

5. The isolated antibody or antigen-binding fragment thereof of claim 1, comprising an HCVR having an amino acid sequence of SEQ ID NO: 2 and an LCVR having an amino acid sequence of SEQ ID NO: 10.

6. The isolated antibody or antigen-binding fragment thereof of claim 1, comprising an HCVR having an amino acid sequence of SEQ ID NO: 18 and an LCVR having an amino acid sequence of SEQ ID NO: 26.

7. The isolated antibody or antigen-binding fragment thereof of claim 1, comprising:
an HCDR1 comprising an amino acid sequence of SEQ ID NO: 36; an HCDR2 comprising an amino acid sequence of SEQ ID NO: 38; an HCDR3 comprising an amino acid sequence of SEQ ID NO: 40; an LCDR1 comprising an amino acid sequence of SEQ ID NO: 44; an LCDR2 comprising an amino acid sequence of SEQ ID NO: 46; and an LCDR3 comprising an amino acid sequence of SEQ ID NO: 48.

8. The isolated antibody or antigen-binding fragment thereof of claim 1, comprising:
an HCDR1 comprising an amino acid sequence of SEQ ID NO: 52; an HCDR2 comprising an amino acid sequence of SEQ ID NO: 54; an HCDR3 comprising an amino acid sequence of SEQ ID NO: 56; an LCDR1 comprising an amino acid sequence of SEQ ID NO: 60; an LCDR2 comprising an amino acid sequence of SEQ ID NO: 62 and an LCDR3 comprising an amino acid sequence of SEQ ID NO: 64.

9. The isolated antibody or antigen-binding fragment thereof of claim 1, comprising:
an HCDR1 comprising an amino acid sequence of SEQ ID NO: 4; an HCDR2 comprising an amino acid sequence of SEQ ID NO: 6; an HCDR3 comprising an amino acid sequence of SEQ ID NO: 8; an LCDR1 comprising an amino acid sequence of SEQ ID NO: 12; an LCDR2 comprising an amino acid sequence of SEQ ID NO: 14; and an LCDR3 comprising an amino acid sequence of SEQ ID NO: 16.

10. The isolated antibody or antigen-binding fragment thereof of claim 1, comprising:
an HCDR1 comprising an amino acid sequence of SEQ ID NO: 20; an HCDR2 comprising an amino acid sequence of SEQ ID NO: 22; an HCDR3 comprising an amino acid sequence of SEQ ID NO: 24; an LCDR1 comprising an amino acid sequence of SEQ ID NO: 28; an LCDR2 comprising an amino acid sequence of SEQ ID NO: 30; and an LCDR3 comprising an amino acid sequence of SEQ ID NO: 32.

11. A pharmaceutical composition comprising one or more isolated antibodies or antigen-binding fragments thereof according to claim 1 and a pharmaceutically acceptable carrier or diluent.

12. The pharmaceutical composition of claim 11, wherein the one or more isolated antibodies or antigen-binding fragments thereof comprise the HCVR/LCVR amino acid sequence pair selected from the group consisting SEQ ID NOs: 34/42, 50/58, 2/10, and 18/26.

13. The pharmaceutical composition of claim 12, wherein the one or more isolated antibodies or antigen-binding fragments thereof comprise the HCVR/LCVR amino acid sequence pair selected from the group consisting of SEQ ID NOs: 34/42 and 50/58.

14. The pharmaceutical composition of claim 11, wherein the isolated antibody or antigen binding fragment thereof comprises:
(a) an HCDR1 comprising an amino acid sequence of SEQ ID NO: 36; an HCDR2 comprising an amino acid sequence of SEQ ID NO: 38; an HCDR3 comprising an amino acid sequence of SEQ ID NO: 40; an LCDR1 comprising an amino acid sequence of SEQ ID NO: 44; an LCDR2 comprising an amino acid sequence of SEQ ID NO: 46; and an LCDR3 comprising an amino acid sequence of SEQ ID NO: 48;
(b) an HCDR1 comprising an amino acid sequence of SEQ ID NO: 52; an HCDR2 comprising an amino acid sequence of SEQ ID NO: 54; an HCDR3 comprising an amino acid sequence of SEQ ID NO: 56; an LCDR1 comprising an amino acid sequence of SEQ ID NO: 60; an LCDR2 comprising an amino acid sequence of SEQ ID NO: 62 and an LCDR3 comprising an amino acid sequence of SEQ ID NO: 64;
(c) an HCDR1 comprising an amino acid sequence of SEQ ID NO: 4; an HCDR2 comprising an amino acid sequence of SEQ ID NO: 6; an HCDR3 comprising an amino acid sequence of SEQ ID NO: 8; an LCDR1 comprising an amino acid sequence of SEQ ID NO: 12; an LCDR2 comprising an amino acid sequence of SEQ ID NO: 14; and an LCDR3 comprising an amino acid sequence of SEQ ID NO: 16; or
(d) an HCDR1 comprising an amino acid sequence of SEQ ID NO: 20; an HCDR2 comprising an amino acid sequence of SEQ ID NO: 22; an HCDR3 comprising an amino acid sequence of SEQ ID NO: 24; an LCDR1 comprising an amino acid sequence of SEQ ID NO: 28; an LCDR2 comprising an amino acid sequence of SEQ ID NO: 30; and an LCDR3 comprising an amino acid sequence of SEQ ID NO: 32.

15. A method of decreasing bacterial load in a subject with a *P. aeruginosa* infection, a method of increasing the survival, or the likelihood of survival of a subject suffering from infection with *P. aeruginosa*, or a method of ameliorating or reducing the severity, duration, or frequency of occurrence of at least one symptom of a *P. aeruginosa* infection in a subject, the method comprising therapeutically administering a pharmaceutical composition comprising one or more antibodies of claim 1 to the subject.

16. The method of claim 15, wherein the subject is selected from the group consisting of a subject undergoing surgery, a subject being treated for a major illness, a trauma patient, an intravenous drug user, a subject having severe burns, a subject using a breathing machine, a subject with a catheter, a subject undergoing chemotherapy, a subject having diabetes, a subject with cystic fibrosis, a subject with tuberculosis, a subject with HIV, or a subject with a compromised immune system.

17. The method of claim 15, wherein the antibody or antigen-binding fragment thereof, or the pharmaceutical composition comprising the antibody or antigen-binding fragment thereof, is administered in combination with a second therapeutic agent selected from the group consisting of an antibiotic, an anti-inflammatory drug, and a different antibody to *P. aeruginosa*.

18. The method of claim 15, wherein the antibody or antigen-binding fragment thereof, or the pharmaceutical composition comprising the antibody or antigen-binding fragment thereof, is administered subcutaneously, intravenously, intradermally, intramuscularly, intranasally, or orally.

19. The method of claim 15, wherein the subject has pneumonia, bacteremia, a bone infection, a joint infection, a skin infection, a burn infection, a wound infection, or any combination thereof.

20. The method of claim 15, wherein the *P. aeruginosa* is resistant or partially resistant to an antibiotic.

21. The method of claim 17, wherein the anti-inflammatory is a corticosteroid or non-steroidal anti-inflammatory drug.

22. A method of decreasing bacterial load in a subject with a *P. aeruginosa* infection, a method of increasing the survival, or the likelihood of survival of a subject suffering from infection with *P. aeruginosa*, or a method of ameliorating or reducing the severity, duration, or frequency of occurrence of at least one symptom of a *P. aeruginosa* infection in a subject, the method comprising prophylactically administering a pharmaceutical composition comprising one or more antibodies of claim 1 to the subject.

23. The method of claim 22, wherein the antibody or antigen-binding fragment thereof, or the pharmaceutical composition comprising the antibody or antigen-binding fragment thereof, is administered in combination with a second therapeutic agent selected from the group consisting of an antibiotic, an anti-inflammatory drug, and a different antibody to *P. aeruginosa*.

24. The method of claim 23, wherein the anti-inflammatory is a corticosteroid or non-steroidal anti-inflammatory drug.

25. The method of claim 22, wherein the antibody or antigen-binding fragment thereof, or the pharmaceutical composition comprising the antibody or antigen-binding fragment thereof, is administered subcutaneously, intravenously, intradermally, intramuscularly, intranasally, or orally.

26. The method of claim 22, wherein the subject is selected from the group consisting of a subject undergoing surgery, a subject being treated for a major illness, a trauma patient, an intravenous drug user, a subject having severe burns, a subject using a breathing machine, a subject with a catheter, a subject undergoing chemotherapy, a subject having diabetes, a subject with cystic fibrosis, a subject with tuberculosis, a subject with HIV, or a subject with a compromised immune system.

27. The method of claim 22, wherein the *P. aeruginosa* is resistant or partially resistant to an antibiotic.

\* \* \* \* \*